US009175035B2

(12) United States Patent
Konno et al.

(10) Patent No.: US 9,175,035 B2
(45) Date of Patent: Nov. 3, 2015

(54) OLIGOPEPTIDE SEQUENCE SPECIFICALLY BONDING TO PHENYLBORONIC ACID GROUP

(75) Inventors: Tomohiro Konno, Tokyo (JP); Kazuhiko Ishihara, Tokyo (JP); Hirokazu Nishida, Tokyo (JP)

(73) Assignees: HITACHI, LTD., Tokyo (JP); THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 13/982,755

(22) PCT Filed: Jan. 30, 2012

(86) PCT No.: PCT/JP2012/051933
§ 371 (c)(1),
(2), (4) Date: Sep. 12, 2013

(87) PCT Pub. No.: WO2012/105471
PCT Pub. Date: Aug. 9, 2012

(65) Prior Publication Data
US 2013/0344590 A1    Dec. 26, 2013

(30) Foreign Application Priority Data
Jan. 31, 2011 (JP) ................................ 2011-018163

(51) Int. Cl.
*G01N 33/53* (2006.01)
*A61K 39/21* (2006.01)
*C07K 1/22* (2006.01)
*C07K 17/06* (2006.01)
*C07K 17/08* (2006.01)
*C07K 17/14* (2006.01)
*C12N 9/02* (2006.01)
*G01N 33/543* (2006.01)

(52) U.S. Cl.
CPC . *C07K 1/22* (2013.01); *C07K 17/06* (2013.01); *C07K 17/08* (2013.01); *C07K 17/14* (2013.01); *C12N 9/0069* (2013.01); *G01N 33/54353* (2013.01)

(58) Field of Classification Search
None
See application file for complete search history.

(56) References Cited

U.S. PATENT DOCUMENTS

| 5,763,203 | A | 6/1998 | Ugelstad et al. |
| 7,547,384 | B2 * | 6/2009 | Keenan ......................... 205/778 |
| 8,153,387 | B2 * | 4/2012 | Lin et al. ...................... 435/7.21 |
| 8,846,036 | B2 * | 9/2014 | Birkenmeyer et al. .... 424/130.1 |
| 2010/0249375 | A1 | 9/2010 | Martin et al. |

FOREIGN PATENT DOCUMENTS

| JP | 8-507857 | 8/1996 |
| JP | 2004-534730 | 11/2004 |
| JP | 2005-261313 | 9/2005 |
| JP | 2006-511797 | 4/2006 |
| JP | 2007-525653 | 9/2007 |
| JP | 2009-520949 | 5/2009 |
| WO | WO 94/20858 | 9/1994 |
| WO | 02/056022 A2 | 7/2002 |
| WO | 2004/058946 A2 | 7/2004 |
| WO | 2005/003383 A1 | 1/2005 |
| WO | 2007/059312 A2 | 5/2007 |

OTHER PUBLICATIONS

Matsumoto, et al. (Jun. 26, 2009) "Reactive extraction of diols with phenyl boronic acid and trioctylmethylammonium chloride as coextractants and quantitative structure-property relationship of their extraction behaviors", Journal of Chemical Technology and Biotechnology, 84(11): 1712-16 (Abstract Only), 3 page long printout.*
http://www.geneinfinity.org/images/aapks.jpg, attributed to "Lehninger, Principle of Biochemistry", no author provided, no journal, no volume, no title, no date provided, 1 page download from internet on May 29, 2014.*
http://toxnet.nlm.nih.gov/cgi-bin/sis/search/a?dbs+hsdb:@term+@DOCNO+7903, section "Environmental Fat/ Exposure Summary", downloaded May 29, 2014, by The Toxnet Toxicology Data Network, National Library of Medicine, last revision date Feb. 14, 2012, no author, no journal, no volume, no issue number, no pages, 18 pages long.*
Bornhorst, et al. (2000) "Purification of Proteins Using Polyhistidine Affinity Tags", Methods in Enzymology, 326: 245-54.*
Mason, et al. (2002) "Differential effect of a his tag at the N- and C-termini: functional studies with recombinant human serum transferrin", Biochemistry, 41(3): 9448-54.*
Candeias, et al. (2010) "Boronic Acids and Esters in the Petasis-Borono Mannich Multicomponent Reaction", Chemical Reviews, 110: 6169-93.*
Stefan Lofas et al., Method for site controlled coupling to carboxymethyldextran surfaces in surfaces plasmon resonance sensors, Biosensors & Bioelectronics 10 (1995) 813-822.
Kazuhiko Ishihara et al., Why do phospholipid polymers reduce protein adsorption? 1998 John Wiley & Sons, Inc., J. Biomed Mater Res. 39, 323-330, 1998.
Frank W. Symington, et al., Lyb-82: A New B Cell Antigen Defined and Characterized with a Monoclonal Antibody, Immunogenetics, 16:381-391, 1982.
Stefan Lofas et al., Method for site controlled coupling to carboxymethyldextran surface in surface plasmon resonance sensors, Biosensors & Bioelectronics 10 (1995) 8-3-822.

(Continued)

*Primary Examiner* — Robert M Kelly
(74) *Attorney, Agent, or Firm* — Baker Botts, L.L.P.

(57) ABSTRACT

An object of the present invention is to provide, as a method for immobilizing a protein molecule, protein immobilization method and means in which orientation of a molecule to be immobilized can be controlled, the molecule can be stably immobilized without a complicated process and a chemical group used for immobilization does not affect the activity and the function of the protein. Specifically, the present invention relates to a method for immobilizing a molecule including the steps of forming a labeled molecule by attaching a label peptide sequence comprising a hydroxyl group-containing amino acid to a molecule; and bringing a molecule having a phenylboronic acid group into contact with the labeled molecule, to capture the labeled molecule by the molecule having a phenylboronic acid group.

24 Claims, 15 Drawing Sheets

(56) References Cited

OTHER PUBLICATIONS

Peter Nilsson et al., Real-Time Monitoring of DNA Manipulations Using Biosensor Technology, analytical Biochemistry 224, 400-408 (1995).

Kazuhiko Ishihara et al., Why do phospholipid polymers reduce protein adsorption?John Wiley & son, Inc. 1998.

Tomohiro Konno et al. Temporal and spatially controllable cell encapsulation using a water-soluble phospholipid polymer with phenylboronic acid moiety, Biomaterials 28 (2007) 1770-1777.

Kazuhiko Ishihara et al., Modification of polysulfone with phospholipid polymer for improvement of the blood compatibility. Part 2. Protein adsorption and platelet adhesion, Biomaterials 20 (1999) 1553-1559.

Toru Moro et al., Surface grafting of artificial joints with a biocompatible polymer for preventing periprosthetic osteolysis, nature materials, Nov. 2004, pp. 829-836, vol. 3.

Correspondence from the State Intellectual Property Office of the People's Republic of China issued Aug. 4, 2014 in regards to Chinese Application No. 201280007203.2.

\* cited by examiner

A

B

Serine (Ser; S)   Threonine (Thr; T)   Tyrosine (Tyr; Y)

Fig. 2-1
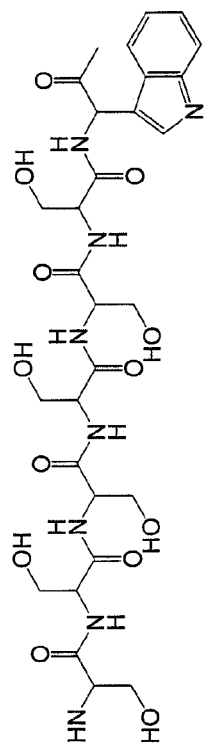
Tyr-Tyr-Tyr-Tyr-Tyr (6Y)(SEQ ID NO. 1)
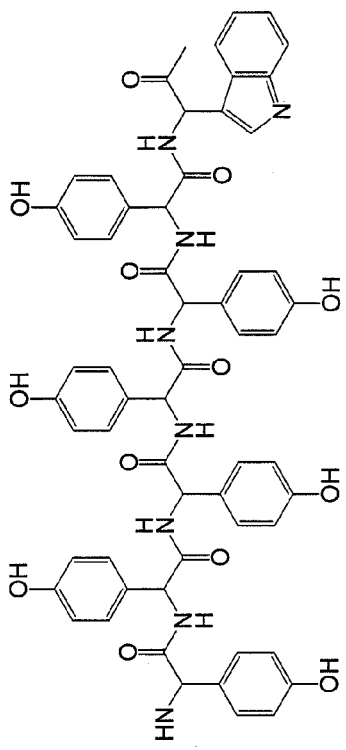
Ser-Ser-Ser-Ser-Ser-Trp (6SW)(SEQ ID NO. 2)
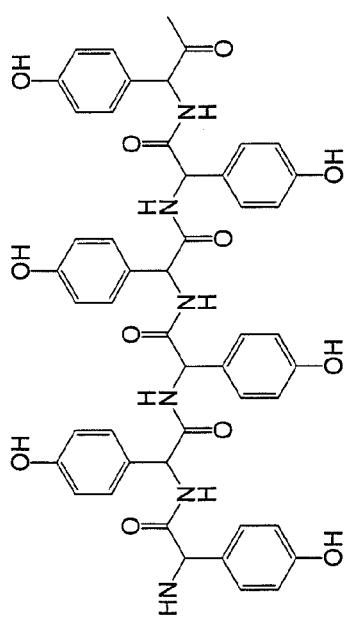
Ser-Ser-Ser-Ser-Trp (4SW)(SEQ ID NO. 3)
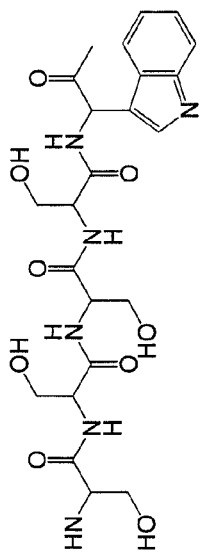
Tyr-Tyr-Tyr-Tyr-Tyr-Trp (6YW)(SEQ ID NO. 4)

Tyr-Tyr-Tyr-Tyr-Tyr-Gly-Gly (6Y2G)(SEQ ID NO. 6)

Tyr-Tyr-Tyr-Tyr-Tyr-Gly-Lys (6YGK)(SEQ ID NO. 8)

Tyr-Tyr-Tyr-Tyr-Trp (4YW)(SEQ ID NO. 5)

Tyr-Tyr-Tyr-Tyr-Tyr-Lys-Lys (6Y2K)(SEQ ID NO. 7)

A

Alizarin red S

No fluorescence

Phosphor
(Excitation light =495nm,
Fluorescence=560nm)

B

PMBV
Poly (MPC-co-BMA-co-VPBA)

Phenylboronic acid group

Fig. 6-1
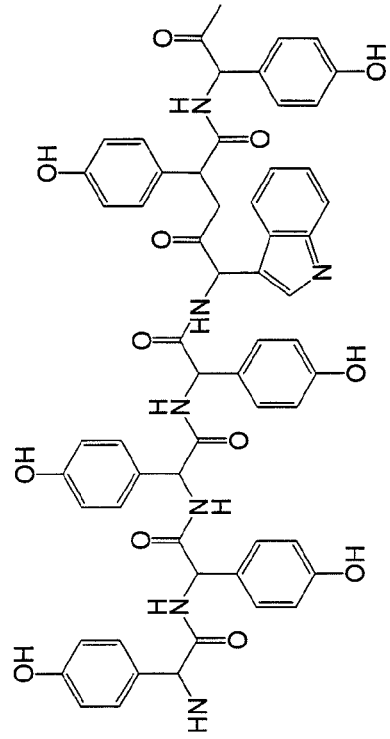
Tyr-Tyr-Tyr-Tyr-Trp-Tyr-Tyr (4YW2Y)(SEQ ID NO. 9)
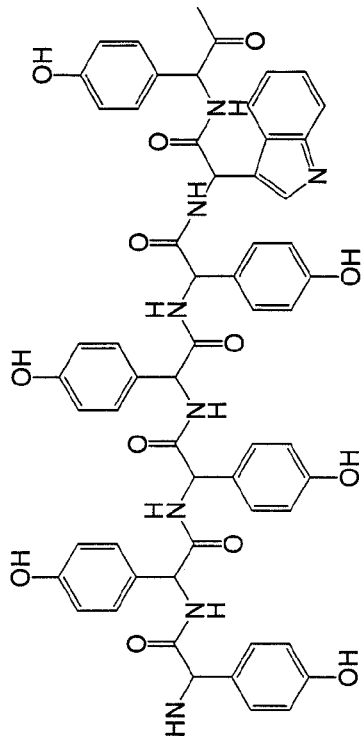
Tyr-Tyr-Tyr-Tyr-Tyr-Trp-Tyr (5YWY)(SEQ ID NO. 11)
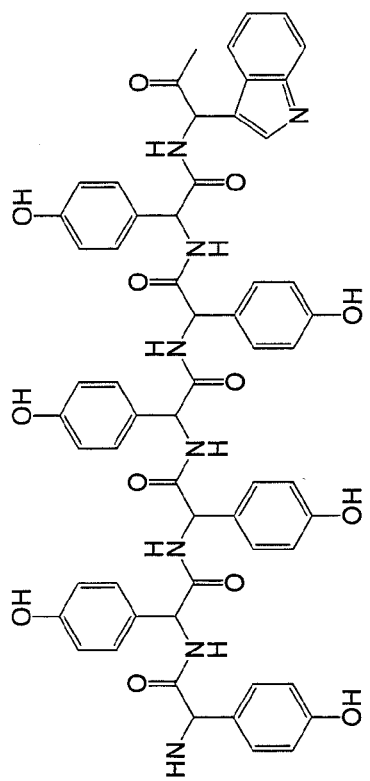
Tyr-Tyr-Tyr-Tyr-Tyr-Tyr-Trp (6YW) (SEQ ID NO. 4)
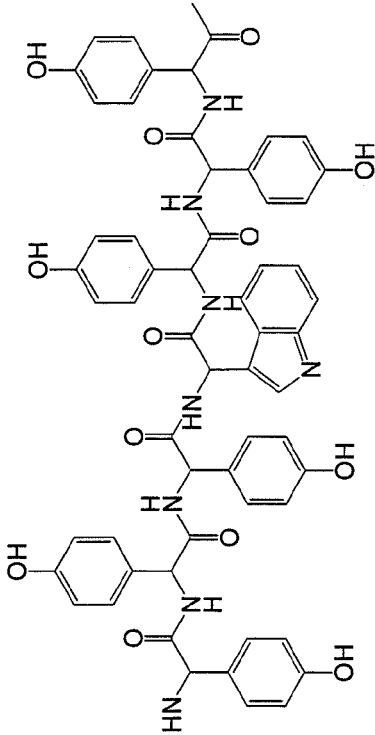
Tyr-Tyr-Trp-Tyr-Tyr-Tyr-Tyr (3YW3Y) (SEQ ID NO. 10)

Tyr-Tyr-Tyr-Tyr-Tyr-Lys-Lys-Trp (6Y2KW)(SEQ ID NO. 12)

Tyr-Tyr-Tyr-Tyr-Tyr-Trp-Lys-Lys (6YW2K)(SEQ ID NO. 13)

A

PMBV

B

PMDV

Fig. 9

OLIGOPEPTIDE SEQUENCE SPECIFICALLY BONDING TO PHENYLBORONIC ACID GROUP

TECHNICAL FIELD

The present invention relates to a method for immobilizing a molecule such as a protein molecule, and more specifically, it relates to a method for immobilizing a molecule by utilizing a molecule having a phenylboronic acid group and a peptide sequence specifically and spontaneously binding to the phenylboronic acid group. Furthermore, the present invention relates to a solid support and an expression vector for use in a method for immobilizing a molecule, and a molecule-immobilized device and a sensor.

BACKGROUND ART

Some protein immobilization methods are conventionally known. In order to industrially utilize enzymes (namely, proteins), some methods for immobilizing protein molecules on various solid supports by forming a bond between a highly reactive side chain of various amino acid residues contained in proteins and a functional group present on a solid support have been developed. Among these methods, widely used methods in which a reaction can be easily caused and a protein molecule can be reacted under gentle conditions without denaturation are an amine coupling method and a surface thiol coupling method.

The amine coupling method is a method in which a carboxyl group precedently immobilized on a solid support is converted into succinimidyl ester by using N-hydroxysuccinimide and 1-ethyl-3-(3-dimethylaminopropyl)-carbodiimide for activation, and a protein is added to be covalently bound thereto via an amino group on the surface of the protein molecule (Non Patent Literature 1).

The surface thiol coupling method is a method in which a thiol group is precedently introduced onto a solid support via a spacer, and an activated protein is added thereto to be covalently bound (Non Patent Literature 2). Specifically, this method is performed as follows: First, a carboxyl group of a protein molecule is allowed to react with 2-(2-pyridinyldithio)ethylamine in the presence of 1-ethyl-3-(3-dimethylaminopropyl)carbodiimide, so as to be converted into a derivative having an active disulfide bond. Next, cystamine is added to a solid support having been activated by the same method as in the amine coupling method and subsequently reduced to be derivatized to a thiol group. The precedently derivatized protein is added to this solid support for forming a covalent bond through disulfide exchange, and thus, immobilization is completed.

In both of the amine coupling method and the surface thiol coupling method, a specific chemical group (that is, an amino group (—$NH_2$) in the amine coupling method and a thiol group (—SH) in the surface thiol coupling method) is used for the immobilization, and for immobilizing a protein molecule, the chemical group on an immobilization substrate is reacted with a functional group of a specific amino acid side chain of the protein molecule. Since a typical eucaryote-derived protein molecule has a molecular weight of approximately 50,000, 400 to 500 amino acid residues are contained therein, and accordingly, multiple amino acids of the same type are present in various directions on the surface of the molecule. Therefore, when a protein molecule is immobilized, the molecule orientation is ununiform. Accordingly, a protein may be immobilized in orientation unsuitable to an interaction analysis subsequently performed or an enzyme reaction performed on the solid support in many cases.

In order to avoid such ununiformity in the orientation occurring in the immobilization, an immobilization method utilizing a specific interaction between biopolymers has been developed (Non Patent Literature 3). A system applying an avidin-biotin interaction is put to practical use widely because these molecules are stable and spontaneously bound to each other in the vicinity of a neutral pH. The crystal structure of an avidin-biotin complex has already been elucidated, and the pattern of the interaction at the atomic level has been clarified.

It has been found, based on a three-dimensional structure of a complex in which a biotin molecule is bound to the base protein avidin, that the biotin molecule is bound to a widely exposed region on the surface of the avidin molecule. Therefore, the function of a macromolecule (such as a protein molecule) modified by the biotin molecule is not inhibited by steric exclusion, which is one of reasons why this method has been widely applied. Furthermore, since a biotinylation sequence can be introduced to a specific position in a protein molecule, the molecule orientation can be made uniform in the immobilization of the protein molecule.

In this method, however, it is necessary to modify a target molecule (protein) with biotin prior to the immobilization, and in addition, it is also necessary to precedently immobilize an avidin molecule somehow on a solid support on which the protein is to be immobilized, and thus complicated processes are required. Furthermore, it is necessary to introduce, for biotin modification, an amino acid sequence of more than ten residues into a target protein, which may damage the essential function of the target protein. Moreover, since it is necessary to immobilize a macromolecule like avidin on a solid support, the molecular weight involved in the whole system is increased, and therefore, if it is necessary to measure charge transfer or slight molecular weight change after the immobilization, this method is not suitably employed.

As an immobilization method in which the orientation of a protein molecule on a solid support can be controlled and merely small change in molecular weight is caused by a chemical group introduced into a system, a method utilizing a histidine tag can be employed (Patent Literatures 1 to 3). A histidine tag is a peptide sequence containing 4 to 6 histidine residues, and this site can be used for chelating a metal ion. Since this sequence can be introduced to any position in a protein molecule, the orientation of the protein molecule can be controlled in the immobilization onto a solid support. Furthermore, since the peptide sequence contains 4 to 6 residues and the molecular weight of a cyclic ligand holding a metal ion on the solid support is approximately 200 at most, the increase in molecular weight in the whole system is small.

In the method utilizing a histidine tag, however, since a coordinate bond formed by chelating a metal ion is employed for binding, the bond stability and the bond strength are lower than those of a covalent bond, and hence, the bond is liable to be affected by pH change or ambient salt concentration change and can be easily dissociated. The stability as a solid support for use in protein immobilization is poorer than that attained in the aforementioned three methods.

Besides, a method in which a polypeptide having unnatural amino acid incorporated therein and a molecule having a functional group specifically interacting with a side chain of the unnatural amino acid are used for detecting the polypeptide (Patent Literature 4), and a method in which a polypeptide having unnatural amino acid incorporated therein is attached to a solid support via the unnatural amino acid (Patent Literature 5) to prepare a solid support-binding protein have been reported.

On the other hand, poly((2-methacryloyloxyethyl phosphorylcholine)-co-(n-butyl methacrylate)-co-(p-vinyl phenylboronic acid)) (hereinafter designated as "PMBV") is a polymer consisting of three units. The respective units are designated as MPC, BMA and VPBA, and play individual roles.

A phosphorykholine group of the MPC unit is known as one of hydrophilic groups present in a lipid bilayer of a cell membrane in vivo. Since a lipid bilayer forms a boundary (cell membrane) of a liquid-liquid interface in vivo, most biopolymers are made not to be adsorbed non-specifically onto this boundary surface. In this manner, the MPC unit prevents a biopolymer such as a protein from being non-specifically adsorbed onto the PMBV polymer, and thus plays a role to improve biocompatibility of a substrate coated with the PMBV polymer (Non Patent Literature 4).

The BMA unit plays a role to suppress too much increase of the polymerization speed in polymer synthesis. Furthermore, since the MPC and the VPBA are extremely hydrophilic (MPC) and hydrophobic (VPBA), if merely the MPC and the VPBA are contained, formation of a granular aggregate having the MPC disposed outside and the VPBA disposed inside is accelerated. Since the BMA has, however, an intermediate hydrophilicity between the MPC and the VPBA, the BMA plays, when added, a role to suppress the formation of the aggregate and to uniformly develop the polymer in an aqueous solution.

The VPBA unit is an active residue having a reaction activity to form a covalent bond with another molecule. The PMBV polymer has a function to increase the biocompatibility of a substrate as a coating agent by itself. When reacted with another polymer, however, it may be processed into a gel or a sheet, so as to be used by itself as a biocompatible substrate. Here, if the PMBV polymer is reacted with a polymer, such as polyvinyl alcohol (PVA), having a flexible structure in which a plurality of —OH groups contained in a molecule can be close to one another within a given distance, a boronic acid group contained in the VPBA is reacted with the plural —OH groups, so that a bivalent covalent bond can be formed. In this manner, the PMBV can be easily processed into the form of a gel or a sheet when reacted with the PVA, and the moisture content and the hardness can be adjusted by changing the composition ratio among the respective units in the PMBV (Non Patent Literature 5).

An MPC polymer containing the MPC as one component is used for coating an artificial vessel or an artificial joint by utilizing its bioinert characteristics owing to a phosphorylcholine group derived from a cell membrane component, and thus, the coated artificial vessel or joint can be used for a long period of time (Non Patent Literatures 6 and 7). By using its property of being easy to form a gel through a reaction with the PVA or the like, application to a technique to independently culture individual cells within a gel has started (Non Patent Literature 5). This technique is expected as indispensable elemental technology for single cell analysis presumed to be widely spread in the future.

CITATION LIST

Patent Literature

Patent Literature 1: WO2005/003383
Patent Literature 2: JP Patent Publication (Kokai) No. 2005-261313
Patent Literature 3: WO2002/056022
Patent Literature 4: WO2007/059312
Patent Literature 5: WO2004/058946

Non Patent Literature

Non Patent Literature 1: Symigton F. W, et al., Immunogenetics, 16:381-391, 1982
Non Patent Literature 2: Lofas S., et al., Biosensors & Bioelectronics, 10:813-822, 1995
Non Patent Literature 3: Nilsson P., et al., Anal. Biochem., 224: 400-408, 1995
Non Patent Literature 4: Ishihara K., et al., J. Biomed. Mater. Res., 39:323-330, 1998
Non Patent Literature 5: Konno T., et al., Biomaterials, 28:1770-1777, 2007
Non Patent Literature 6: Ishihara K., et al., Biomaterials, 20:1553-1559, 1999
Non Patent Literature 7: Moro T., et al., Nature Mater., 3-829-836, 2004

SUMMARY OF INVENTION

Technical Problem

An object of the present invention is to provide protein immobilization method and means in which a protein molecule to be immobilized can be controlled in its orientation in immobilizing the molecule and can be stably immobilized without a complicated process and the activity and the function of the protein are not affected by a chemical group used for the immobilization.

Solution to Problem

The present inventor has made earnest studies for solving the aforementioned problems, resulting in finding that a peptide sequence comprising a hydroxyl group-containing amino acid forms a stable covalent bond with a phenylboronic acid, and hence a molecule such as a protein molecule can be immobilized by using this peptide sequence and a molecule having a phenylboronic acid group. Furthermore, the present inventor has found: (i) that orientation of a protein molecule in immobilization can be controlled by introducing the peptide sequence to a specific position in the protein molecule; (ii) that a precedent complicated process can be omitted by precedently introducing the peptide sequence necessary for immobilization into the molecule; and (iii) that increase in molecular weight involved in binding can be controlled because a chemical group (a linker) involved in the binding reaction are the molecule having a phenylboronic acid group having a molecular weight of approximately several hundred and the peptide sequence set to have a molecular weight of several hundred to one thousand and several hundred. The present invention was achieved on the basis of these findings for solving the aforementioned conventional problems.

Accordingly, the present invention provides the following:
[1] A method for immobilizing a molecule, comprising the steps of attaching a label peptide sequence comprising a hydroxyl group-containing amino acid to a molecule to form a labeled molecule; and bringing a molecule having a phenylboronic acid group into contact with the labeled molecule, to capture the labeled molecule by the molecule having a phenylboronic acid group.

[2] The method according to [1], wherein the label peptide sequence is a peptide sequence comprising two or more residues of hydroxyl group-containing amino acids.

[3] The method according to [1] or [2], wherein the hydroxyl group-containing amino acid is one or more selected from the group consisting of serine, threonine and tyrosine.

[4] The method according to any one of [1] to [3], wherein the label peptide sequence comprises, in addition to the hydroxyl group-containing amino acid, 1 to 3 residues of basic amino acids.

[5] The method according to [4], wherein the basic amino acids are one or more selected from the group consisting of lysine, arginine and tryptophan.

[6] The method according to any one of [1] to [5], wherein the label peptide sequence consists of consecutive 4 to 6 residues of hydroxyl group-containing amino acids; or consists of 3 to 5 residues of hydroxyl group-containing amino acids and 1 to 3 residues of basic amino acids that are 4 to 6 residues in total of amino acids.

[7] The method according to any one of [1] to [5], wherein the label peptide sequence consists of consecutive 7 or more residues of hydroxyl group-containing amino acids; or consists of 4 or more residues of hydroxyl group-containing amino acids and 1 to 3 residues of basic amino acids that are 7 or more residues in total of amino acids.

[8] The method according to any one of [1] to [7], wherein the molecule is a protein.

[9] The method according to any one of [1] to [8], wherein the label peptide sequence is attached to the molecule via a covalent bond in a position away from an active site or a recognition region of the molecule.

[10] The method according to any one of [1] to [9], wherein the molecule having a phenylboronic acid group is a polymer having two or more phenylboronic acid groups.

[11] The method according to any one of [1] to [10], wherein the molecule having a phenylboronic acid group is poly((2-methacryloyloxyethyl phosphorylcholine)-co-(n-butyl methacrylate)-co-(p-vinyl phenylboronic acid)) or poly((2-methacryloyloxyethyl phosphorylcholine)-co-(dimethylaminoethyl methacrylate)-co-(p-vinyl phenylboronic acid)).

[12] The method according to any one of [1] to [11], wherein the molecule having a phenylboronic acid group is bound to a solid support.

[13] The method according to any one of [1] to [12], wherein the molecule having a phenylboronic acid group is bound to a surface of a solid support and the molecule is immobilized on the surface of the solid support.

[14] The method according to [13], wherein the molecule is immobilized as a monomolecular layer held on the surface of the solid support in the same orientation.

[15] The method according to any one of [12] to [14], wherein the molecule having a phenylboronic acid group comprises a phenylboronic acid group and a headgroup, and the headgroup is a functional group capable of covalently binding to the solid support.

[16] The method according to any one of [12] to [15], wherein the solid support is a noble metal.

[17] The method according to [16], wherein the noble metal is selected from the group consisting of silver, gold, platinum and palladium.

[18] The method according to any one of [12] to [15], wherein the solid support is an electrode.

[19] The method according to any one of [12] to [15], wherein the solid support is a plastic.

[20] The method according to [19], wherein the plastic is selected from the group consisting of polycarbonate, polyethylene, polypropylene, polystyrene, polyvinyl chloride and polyethylene terephthalate.

[21] The method according to any one of [12] to [20], wherein the molecule having a phenylboronic acid group is bound to the solid support directly or via a spacer sequence.

[22] The method according to any one of [1] to [11], wherein the molecule having a phenylboronic acid group is crosslinked by a bridging molecule to form an immobilization substrate, and the molecule is immobilized on the immobilization substrate.

[23] The method according to [22], wherein the bridging molecule is polyhydric alcohol.

[24] The method according to [23], wherein the polyhydric alcohol is polyvinyl alcohol.

[25] The method according to any one of [22] to [24], wherein the immobilization substrate is one or more selected from the group consisting of a solid, a polymer membrane, a polymer semipermeable membrane, a solid phase gel and a liquid phase gel.

[26] A solid support for immobilizing a molecule, wherein the solid support has a molecule having a phenylboronic acid group bound to a surface of the solid support.

[27] An expression vector for expressing a fusion protein with a label peptide sequence, comprising a DNA encoding a label peptide sequence comprising a hydroxyl group-containing amino acid; and a cassette for insertion of a DNA encoding a protein molecule.

[28] A molecule-immobilized device, in which a molecule attached to a label peptide sequence comprising a hydroxyl group-containing amino acid is immobilized on a solid support via a molecule having a phenylboronic acid group.

[29] A molecule-immobilized device, in which a molecule attached to a label peptide sequence comprising a hydroxyl group-containing amino acid is immobilized on an immobilization substrate via a molecule having a phenylboronic acid group and the immobilization substrate is formed by crosslinking the molecule having a phenylboronic acid group by a bridging molecule.

[30] A sensor comprising a molecule-immobilized device according to [28] or [29]; and means for detecting an intermolecular interaction.

Advantageous Effects of Invention

The present invention provides molecule immobilization method and means. In the present method and means, since a peptide sequence necessary for immobilization can be introduced to an any site of a molecule (such as a protein molecule), the orientation of the molecule on a solid support can be controlled. Furthermore, since a binding reaction for immobilizing the molecule spontaneously occurs in the vicinity of a neutral pH, there is no need to perform a pretreatment. Since the peptide sequence to be introduced into the molecule to be immobilized can be adjusted to contain 5 to 8 amino acid residues, change in the molecular weight in the whole system is small. Moreover, since the bond to be formed in the immobilization is a covalent bond, the molecule immobilization is stable against pH change and salt concentration change.

Other objects, features and advantages of the present invention will be apparent from the following detailed description of preferred embodiments of the invention.

BRIEF DESCRIPTION OF DRAWINGS

FIG. 2-1 is a list of chemical structural formulas of synthetic peptides used for screening for a peptide sequence binding to a phenylboronic acid group.

FIG. 2-2 is a list of chemical structural formulas of synthetic peptides used for screening for a peptide sequence binding to a phenylboronic acid group.

FIG. 6-1 is a list of chemical structural formulas of synthetic peptides used for optimizing a peptide sequence binding to a phenylboronic acid group.

FIG. 6-2 is a list of chemical structural formulas of synthetic peptides used for optimizing a peptide sequence binding to a phenylboronic acid group.

FIG. 9 is a bar chart illustrating how much the various synthetic peptides inhibit a reaction between a phenylboronic acid-specifically binding dye and a phenylboronic acid group, performed by using the phenylboronic acid group-containing polymer PMBV (in FIG. 9A) or PMDV (in FIG. 9B).

DESCRIPTION OF EMBODIMENTS

Now, the present invention will be described in detail. This application is based upon and claims the benefit of priority of JP Patent Application No. 2011-018163, filed on Jan. 31, 2011, the entire contents of the description and/or drawings of which are incorporated herein by reference.

Figure 1:
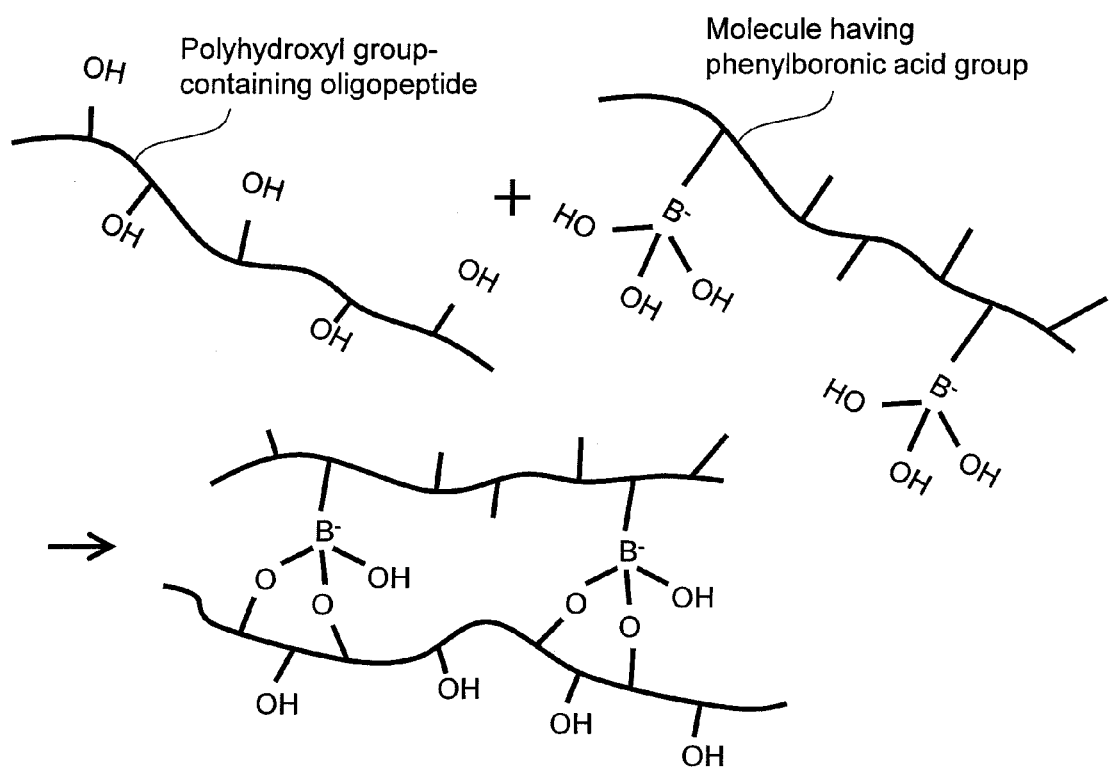
FIG. 1 illustrates a conceptual diagram of a bond between a molecule having a phenylboronic acid group and a polyhydroxyl group-containing oligopeptide (in FIG. 1A), and chemical structural formulas of hydroxyl group-containing amino acids (in FIG. 1B), in which three letter codes and single letter codes of the amino acid are given in parentheses.
Figure 1:
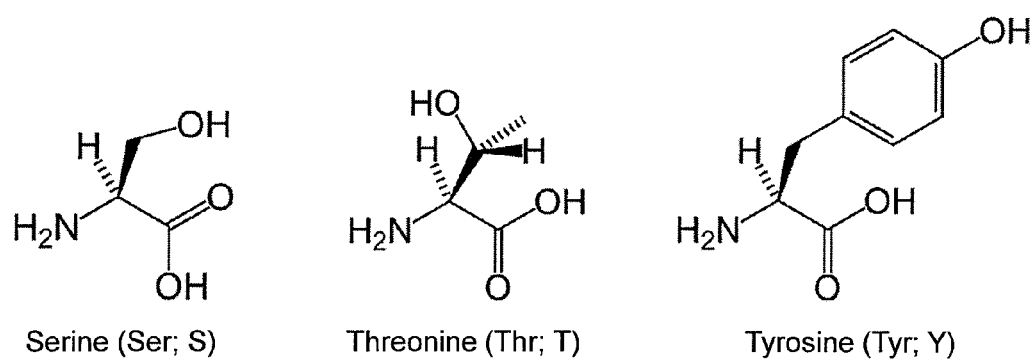

The present invention relates to immobilization of a molecule labeled with a peptide sequence comprising a hydroxyl group-containing amino acid by using, as a linker, a molecule having a phenylboronic acid group on the basis of the characteristic of a phenylboronic acid group that it is stabilized by a covalent bond between its hydroxyl group and a hydroxyl group contained in another molecule. Specifically, a hydroxyl group contained in a phenylboronic acid group covalently binds to two hydroxyl groups present in a peptide sequence comprising hydroxyl group-containing amino acids under slightly basic to basic conditions (FIG. 1A). Accordingly, when a hydroxyl group-containing amino acid as exemplarily illustrated in FIG. 1B is incorporated into a label peptide sequence, a label peptide sequence specifically and spontaneously binding to a molecule having a phenylboronic acid group can be obtained. Such a label peptide sequence has a sequence minimally found in proteins present in nature, and can be easily inserted into or added to any protein molecule by a genetic engineering method.

In the present invention, a "label peptide sequence" refers to a peptide sequence capable of binding to a molecule having a phenylboronic acid group to be used as a linker for immobilizing a molecule, and is also designated as an "oligopeptide sequence". The label peptide sequence is not especially limited in its length and composition (arrangement) as long as it has an amino acid containing a hydroxyl group as a side chain, namely, a hydroxyl group-containing amino acid. Preferable examples of the hydroxyl group-containing amino acid include serine (Ser, S), threonine (Thr, T) and tyrosine (Tyr, Y), and the label peptide sequence can contain one or a plurality of these. The label peptide sequence preferably contains tyrosine as the hydroxyl group-containing amino acid.

In the present invention, in order that the label peptide sequence has efficient binding capacity to phenylboronic acid, it is necessary for two hydroxyl groups to be sterically close to each other so as to supply a phenylboronic acid group with a hydroxyl group (FIG. 1A). Therefore, the label peptide sequence preferably contains two or more hydroxyl group-containing amino acids. In the primary sequence of the label peptide sequence, two hydroxyl group-containing amino acids adjacent to each other or two hydroxyl group-containing amino acids arranged with one residue of amino acid sandwiched therebetween may be, in some cases, difficult to take conformation of hydroxyl groups suitable to form a bond with phenylboronic acid. Therefore, in order to increase the number of pairs of hydroxyl groups that can be made to come close to a phenylboronic acid group, the label peptide sequence is preferably a peptide sequence containing consecutive 4 to 6 residues of hydroxyl group-containing amino acids. Alternatively, the label peptide sequence may be a peptide sequence consisting of consecutive 7 or more (for example, 7 to 50) residues of hydroxyl group-containing amino acids, but as the number of consecutive hydroxyl group-containing amino acids is larger, there is more possibilities that the structural formation or the activity of a molecule to be attached to the label peptide sequence are affected.

Therefore, the label peptide sequence is preferably designed in consideration of this affection.

Furthermore, a hydroxyl group-not-containing amino acid (an amino acid which does not contain hydroxyl group) may be present between two or more hydroxyl group-containing amino acids, or a hydroxyl group-not-containing amino acid may be added to an end of a hydroxyl group-containing amino acid. For example, a peptide sequence containing 2 or more residues of arbitrary amino acids sandwiched between 2 hydroxyl group-containing amino acid residues present at both ends may be used.

Moreover, it has been found that the local pH of a site where a binding reaction occurs is preferably basic for increasing the binding efficiency to phenylboronic acid. Therefore, it is preferable, in the label peptide sequence, that 1 to 4 (preferably 1 to 3) residues of basic amino acids are adjacent to the above-described consecutive hydroxyl group-containing amino acids or inserted to a sequence of the consecutive hydroxyl group-containing amino acids. Here, a basic amino acid means an amino acid selected from the group consisting of lysine (Lys, K), arginine (Arg, R) and tryptophan (Trp, W), and the label peptide sequence may contain one or a plurality of these. Examples of the label peptide sequence include a peptide sequence consisting of 3 to 5 residues of hydroxyl group-containing amino acids and 1 to 3 residues of basic amino acids that are 4 to 6 residues in total of amino acids, and a peptide sequence consisting of 4 or more residues of hydroxyl group-containing amino acids and 1 to 3 residues of basic amino acids that are 7 or more residues in total of amino acids.

Specific examples of the label peptide sequence are as follows:

Tyr-Tyr-Tyr-Tyr-Tyr-Tyr (6Y) (SEQ ID NO: 1)

Ser-Ser-Ser-Ser-Ser-Ser-Trp (6SW) (SEQ ID NO: 2)

Ser-Ser-Ser-Ser-Trp (4SW) (SEQ ID NO: 3)

Tyr-Tyr-Tyr-Tyr-Tyr-Trp (6YW) (SEQ ID NO: 4)

Tyr-Tyr-Tyr-Tyr-Trp (4YW) (SEQ ID NO: 5)

Tyr-Tyr-Tyr-Tyr-Tyr-Try-Gly-Gly (6Y2G) (SEQ ID NO: 6)

Tyr-Tyr-Tyr-Tyr-Tyr-Lys-Lys (6Y2K) (SEQ ID NO: 7)

Tyr-Tyr-Tyr-Tyr-Tyr-Gly-Lys (6YGK) (SEQ ID NO: 8)

Tyr-Tyr-Tyr-Tyr-Trp-Tyr-Tyr (4YW2Y) (SEQ ID NO: 9)

Tyr-Tyr-Tyr-Trp-Tyr-Tyr-Tyr (3YW3Y) (SEQ ID NO: 10)

Tyr-Tyr-Tyr-Tyr-Tyr-Trp-Tyr (5YWY) (SEQ ID NO: 11)

Tyr-Tyr-Tyr-Tyr-Tyr-Lys-Lys-Trp (6Y2KW) (SEQ ID NO: 12)

Tyr-Tyr-Tyr-Tyr-Tyr-Trp-Lys-Lys (6YW2K) (SEQ ID NO: 13)

In the present invention, the label peptide sequence described above is attached to a molecule, thereby forming a labeled molecule. Here, a "molecule" may be any molecule as long as it is desired to be immobilized, and examples of the molecule include proteins (such as a peptide and a polypeptide) and a gold particle when cysteine or the like is introduced into the label peptide sequence. In the present invention, a protein molecule is preferably employed as a target because the label peptide sequence can be easily and efficiently attached thereto and it is particularly demanded to be immobilized. Examples of the protein include an enzyme, a receptor, an antibody, an antigen, a filament-forming protein such as actin or kinesin, and a part or a subunit of these.

The label peptide sequence may be attached to any site of a molecule. However, the label peptide sequence is preferably attached to a molecule via a covalent bond in a position away from an active site or a recognition region of the molecule so as not to affect the tertiary structure or the activity of the target molecule.

Furthermore, the label peptide sequence can be attached to a molecule by any of methods and means known in this technical field. If a protein molecule is to be immobilized, for example, the label peptide sequence can be attached to the protein molecule by producing the protein molecule as a fusion protein with the label peptide sequence.

A method for preparing a fusion protein is known in this technical field, and examples of the method include chemical synthesis and gene recombination. In the chemical synthesis, a fusion protein can be prepared in accordance with a known peptide synthesizing method by using, for example, a commercially available peptide synthesizer or a commercially available peptide synthesis kit. In the gene recombination, for example, a DNA encoding a target protein molecule and a DNA encoding the label peptide sequence are linked to each other directly or via a linker sequence, the linked DNAs are inserted to a known vector such as a plasmid, the resulting vector is introduced into a host cell, and thus, a fusion protein (labeled molecule) can be expressed in the host cell. The label peptide sequence is preferably added to a carboxyl terminal and/or an amino terminal of a protein molecule. The carboxyl terminal or the amino terminal of a protein molecule is occasionally protruded, as an end point of the molecule, to a solvent accessible region, and therefore, if the label peptide sequence is added to such a terminal, influence on the formation of the correct three-dimensional structure of the protein can be suppressed as well as inhibition of the essential function of the protein can be suppressed.

Furthermore, in adding the label peptide sequence to the carboxyl terminal and/or the amino terminal of a protein molecule, a linker sequence consisting of several resides is preferably added to the amino terminal side of the label peptide sequence if it is added to the carboxyl terminal or to the carboxyl terminal side of the label peptide sequence if it is added to the amino terminal, so that possibility of the functional inhibition of the protein can be further reduced. The linker sequence to be inserted between the protein molecule and the label peptide sequence may be a linker sequence known in this technical field, and for example, a linker sequence consisting of 1 to 20 amino acids, preferably 1 to 10 amino acids and more preferably 2 to 6 amino acids can be used. More specifically, approximately 4 to 6 consecutive glycine residues having an advantage of a high degree of freedom in the conformation can be used as the linker sequence.

As the vector used for expressing a fusion protein, any one of known vectors including a plasmid, a phagemid, a vector derived from a virus (such as an animal virus vector derived from a retrovirus, an adenovirus or a vaccinia virus, or an insect virus vector derived from baculovirus) and artificial chromosomes can be used. An expression vector for expressing a fusion protein can be obtained by linking a DNA encoding a protein molecule and a DNA encoding the label peptide sequence to a vector so as to express the fusion protein. Incidentally, a promoter or a transcription termination signal, and if desired, an enhancer, a splicing signal, a poly A addition signal, a selected marker or the like are preferably linked to the expression vector.

Figure 10:
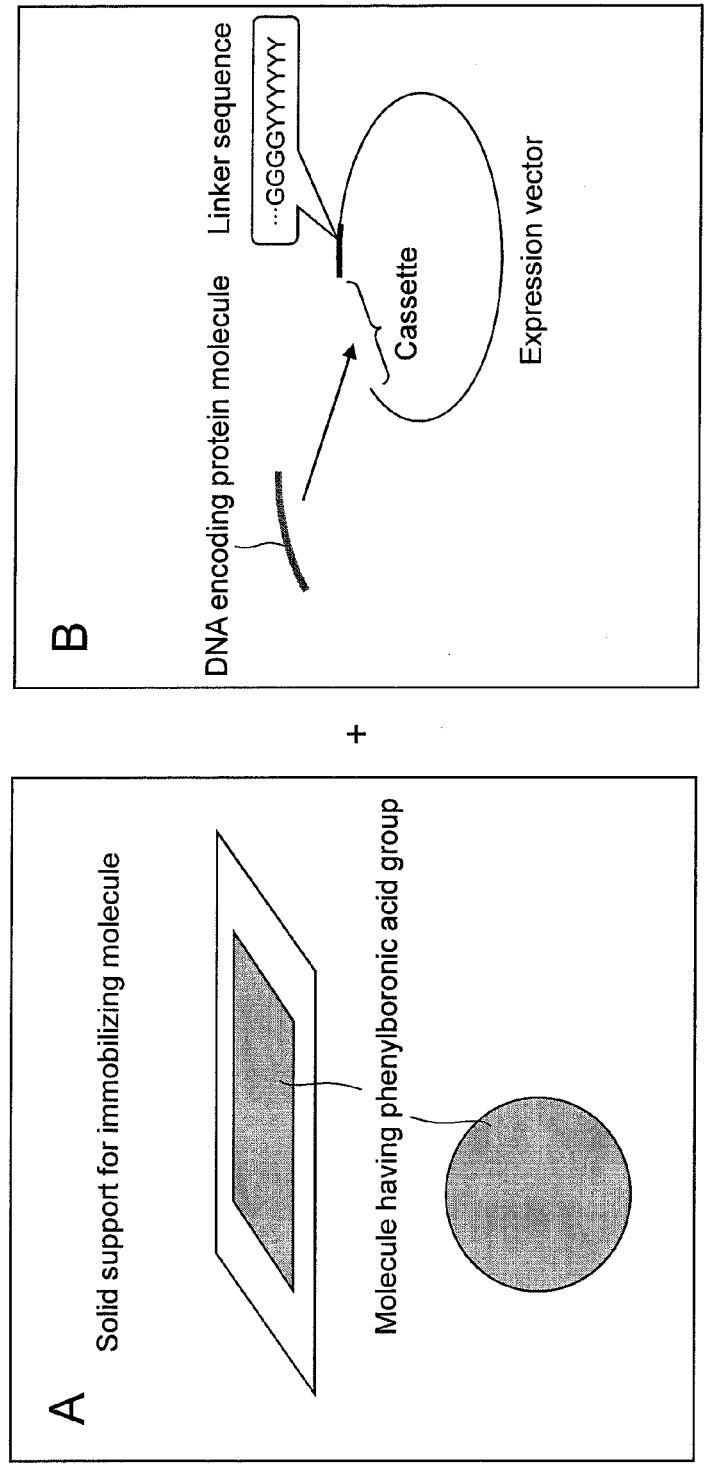
FIG. 10 illustrates the outline of a solid support, for use in immobilization of a protein molecule, to which a molecule having a phenylboronic acid group is bound (in FIG. 10A), and the outline of an expression vector used for producing a fusion protein with a label peptide sequence (in FIG. 10B).

In the present invention, in order to easily and efficiently prepare a protein molecule attached to the label peptide sequence as a fusion protein, an expression vector containing a DNA encoding the label peptide sequence and a cassette for insertion of a DNA encoding the protein molecule can be used (FIG. 10B). If such an expression vector is used, an expression vector for expressing the fusion protein with the label peptide sequence can be constructed merely by inserting the DNA encoding the protein molecule into the cassette of the expression vector. Accordingly, the expression vector at least contains a DNA encoding the label peptide sequence (for example, the amino acid sequence of any of SEQ ID NOs: 1 to 13) and a cassette (such as a restriction enzyme site or a multicloning site) for inserting a DNA encoding a protein molecule, and may optionally contain a DNA encoding a linker sequence for linking the label peptide sequence and the protein molecule, a control sequence useful for expressing the fusion protein and the like.

The thus constructed expression vector is introduced into a host cell to prepare a transformant. The host cell used for the transformation is not especially limited as long as it can express and produce a fusion protein, and examples include bacteria (such as E. coli), yeast, an animal cell and an insect cell. The expression vector can be introduced into the host cell by any method known in this technical field such as electroporation, the calcium phosphate method or lipofection. The fusion protein can be obtained by cultivation of the transformant and isolation/purification from the culture.

In this manner, the labeled molecule can be obtained by attaching the label peptide sequence to the molecule.

As the molecule having a phenylboronic acid group, any arbitrary molecule can be used as long as it has a phenylboronic acid group (also designated as dihydroxyphenylborane) having boronic acid $(B(OH)_2)$ bound to a phenyl group. It may be, for example, phenylboronic acid, an organic compound having one or more phenylboronic acid groups, or a polymer compound obtained by polymerizing a monomer having a phenylboronic acid group. A polymer having two or more phenylboronic acid groups is preferably used.

The molecule having a phenylboronic acid group may contain, in addition to the phenylboronic acid group, one or more functional groups suitable for the binding reaction with the label peptide sequence, the binding to the solid support and the reaction of an immobilized molecule. Examples of such a functional group include a group that makes basic the local pH of a site where the binding reaction between the phenylboronic acid group and the label peptide sequence occurs (such as a dimethylaminoethyl group or a diethylaminoethyl group), a headgroup that can covalently bind to a solid support (such as a thiol group or a succinimide group), and a functional group that can increase the flow property of the molecule so as to increase the reaction efficiency of the molecule (such as a 2-methacryloyloxyethyl phosphorylcholine).

As a specific example of a polymer molecule having a phenylboronic acid group, poly((2-methacryloyloxyethyl phosphorylcholine)-co-(n-butyl methacrylate)-co-(p-vinyl phenylboronic acid)) (hereinafter abbreviated as PMBV) slightly affects formation of a hydrogen-binding cluster of a water molecule on a solid-liquid interface owing to the function of a 2-methacyloyloxyethyl phosphorylcholine (MPC) group, and therefore, the free water content is high in the vicinity of the interface. Accordingly, when various reactions are to be performed on an interface between a liquid phase and a solid support on which a protein molecule such as an enzyme is immobilized, a diffusion coefficient of other molecules such as an enzyme substrate can be high, and hence, the reaction efficiency of molecules can be expected to be remarkably increased.

Furthermore, poly((2-methacryloyloxyethyl phosphorylcholine)-co-(dimethylaminoethyl methacrylate)-co-(p-vinyl phenylboronic acid)) (hereinafter abbreviated as PMDV), that is, a polymer molecule having a phenylboronic acid group, contains a dimethylamino group as a basic functional group. As described above, the local pH of the site where the binding reaction between the phenylboronic acid group and the label peptide sequence occurs is preferably basic, and therefore, the PMDV can increase the binding activity between the phenylboronic acid group and the label peptide sequence while keeping the above-described effects of the PMBV, so that a molecule can be more efficiently immobilized.

Figure 11:
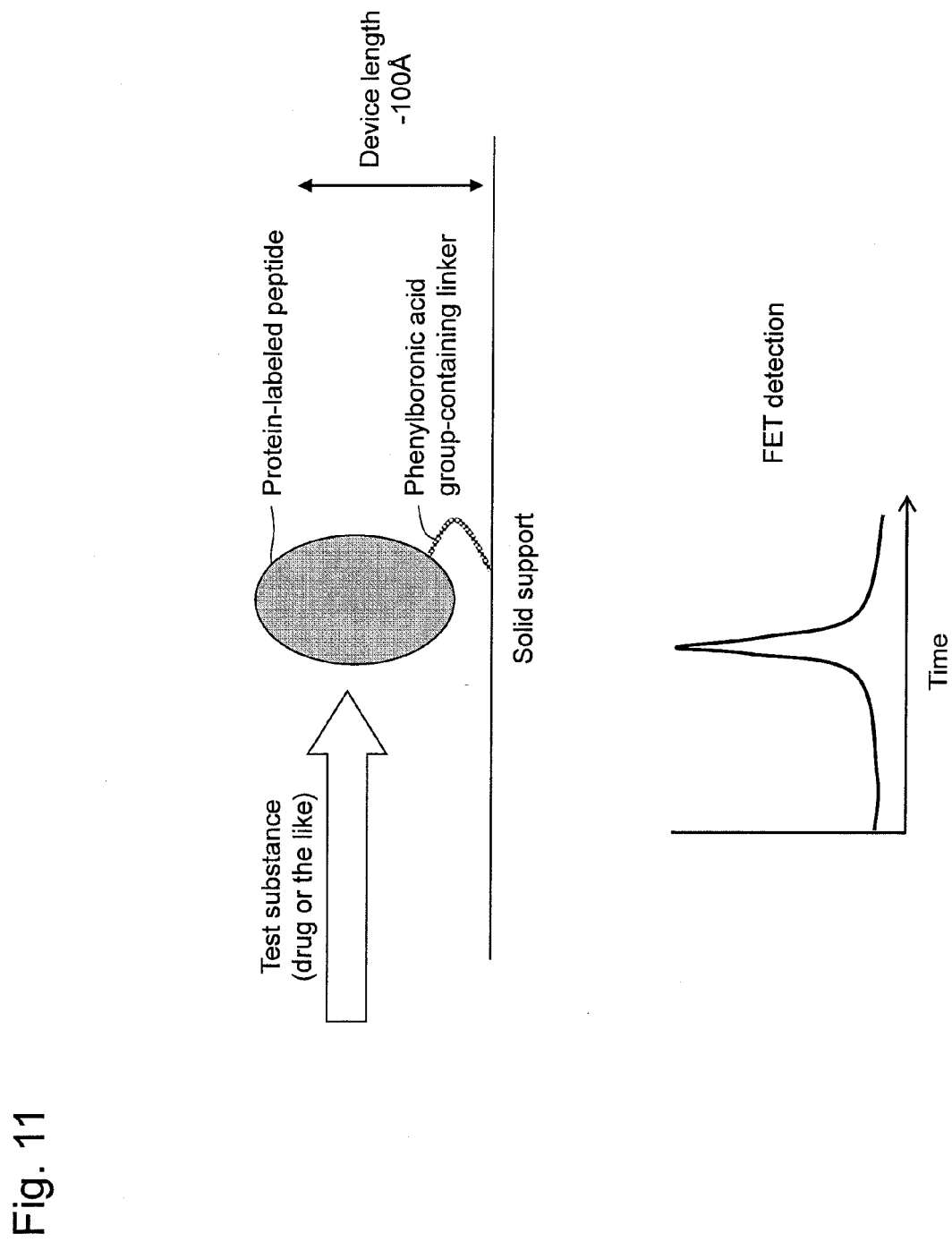
FIG. 11 illustrates an example of a measurement system using a device having a protein immobilized on a solid support via a molecule having a phenylboronic acid group as a linker.

The molecule having a phenylboronic acid group can be bound to a solid support, whereby the target molecule can be immobilized on the solid support (FIG. 11). Preferably, the molecule having a phenylboronic acid group is bound to the surface of the solid support, and the target molecule is immobilized on the surface of the solid support. The solid support to be used is not especially limited as long as it is commonly used in this technical field. Specific examples include metals such as noble metals (including gold, silver, platinum and palladium), copper, aluminum, tungsten, molybdenum, chromium, titanium and nickel; alloys such as stainless steel, hastelloy, inconel, Monel and duralumin; electrodes of semiconductor devices or the like (such as a transistor and an FET); silicon glass materials such as glass, quartz glass, fused quartz, synthetic silica, alumina, sapphire, ceramics, forsterite and photosensitive glass; plastics such as polyester, polystyrene, polyethylene, polypropylene, nylon, acrylic, polycarbonate, polyethylene terephthalate (PET), polyurethane, a phenol resin, a melamine resin, an epoxy resin and polyvinyl chloride; agarose, dextran, cellulose, polyvinyl alcohol, nitrocellulose, chitin and chitosan. Besides, the shape of the solid support is not also especially limited, and examples of the shape include one having a flat plane (such as a titer plate, a porous or microporous array or a microchannel), a plate, a film, a tube and particles (such as magnetic particles).

A method for binding the molecule having a phenylboronic acid group to the solid support is not especially limited. The molecule having a phenylboronic acid group can be bound to the solid support, for example, via a covalent bond or an ionic bond or by physical adsorption. Specifically, the molecule having a phenylboronic acid group can be bound to the surface of a solid support by, for example, applying, to the solid support, a solution of an organic solvent or the like in which the molecule having a phenylboronic acid group is mixed and drying the applied solution. Alternatively, if the molecule having a phenylboronic acid group also contains another functional group, a variety of methods can be selected in accordance with, for example, the properties of the solid support, the properties of a molecule to be immobilized, and the properties of a chemical reaction to be performed on the solid support by using them. The molecule having a phenylboronic acid group may be bound to the solid support via a spacer sequence, such as a hydrocarbon group containing 1 to 10 carbon atoms.

The molecule having a phenylboronic acid group can be bound to the solid support via a covalent bond by, for example, introducing into the solid support a functional group reactive to a headgroup contained in the molecule having a phenylboronic acid group for causing a reaction therebetween. If the molecule having a phenylboronic acid group has a headgroup that can covalently bind to the solid support (such as a noble metal), the headgroup can be used for binding the molecule having a phenylboronic acid group to the noble metal solid support of gold, platinum or the like via a covalent bond. Gold, platinum and the like can be controlled in configuration at the atomic level. In other words, a lattice plane grown as metallic crystal can be processed into a plate shape free from irregularities at a level of even a single atom. When a monomolecular layer of the molecule having a phenylboronic acid group is constructed on such a plane, a plate-shaped solid support capable of capturing the label peptide sequence can be obtained. When a molecule attached to the label peptide sequence is bound to this solid support made of the metal material having the monomolecular layer of the molecule having a phenylboronic acid group, a device in which the molecule is immobilized on the metal plane with its height controlled with an error of several angstroms while controlling the molecule orientation can be provided. For example, target molecules can be immobilized on the surface of a solid support as a monomolecular film wherein molecules are held in the same orientation.

Since a molecule can be thus bound onto a noble metal support such as an electrode with an error of several angstroms while controlling the orientation, the active site of the immobilized molecule (of, for example, a protein, and an enzyme in particular) can be disposed within approximately 100 angstroms from the surface of the noble metal support (eucaryote-derived proteins are said to have an average molecular weight of approximately 50,000, and the maximum molecular length is approximately 100 angstroms). Therefore, an enzyme reaction (involving various charge transfer reactions in many cases) can be caused within a device length of an FET estimated as several tens to one hundred and several tens angstroms, and therefore, a system for detecting any enzyme reaction by using an FET can be constructed.

Furthermore, a covalent bond can be formed by using, for example, an amino group as the headgroup of the molecule having a phenylboronic acid group and introducing an active ester group, an epoxy group, an aldehyde group, a carbodiimide group, an isothiocyanate group or an isocyanate group into a solid support. Alternatively, a thiol group may be used as the headgroup and an active ester group, a maleimide group or a disulfide group may be introduced into a solid support. Examples of the active ester group include a p-nitrophenyl group, an N-hydroxysuccinimide group, a succinimide group, a phthalic imide group and a 5-norbornene-2,3-dicarboxylmide group. One exemplary method for introducing a functional group into a solid phase carrier is a method in which the surface of a solid is treated with a silane coupling agent having a desired functional group (such as gamma-aminopropyltriethoxysilane). Another exemplary method is a plasma treatment.

A specific method for binding the molecule having a phenylboronic acid group to a solid support includes, for example, (i) applying a solution of an organic solvent such as ethanol containing a molecule having a phenylboronic acid group (such as PMBV) onto a surface of, for example, a plastic substrate of polystyrene, polycarbonate, polyvinyl chloride or the like or a metal substrate of gold, platinum, copper or the like, and drying the applied solution, and (ii) adding a solution containing a molecule (a protein or the like) attached to the label peptide sequence to the substrate, thereby obtaining a substrate coated with molecules controlled in the orientation.

In this manner, the molecule having a phenylboronic acid group can be bound to the solid support. The present invention also provides a solid support to the surface of which a molecule having a phenylboronic acid group (of preferably PMBV or PMDV) precedently bound. When this solid support is used, a molecule can be easily and efficiently immobilized on the solid support by simply applying a molecule attached to the label peptide sequence (as exemplarily illustrated in FIG. 10A).

Furthermore, the molecule immobilization is not limited to the immobilization on a solid support. In another preferable method of the present invention, an immobilization substrate can be formed by crosslinking, by using a bridging molecule, a functional group (such as a hydroxyl group) other than a hydroxyl group necessary for binding to the label peptide sequence in the molecule having a phenylboronic acid group. As a result, a target molecule can be immobilized on the immobilization substrate thus formed by crosslinkage. Examples of the bridging molecule used in this method include polyhydric alcohols, such as polyvinyl alcohol, and polysaccharides, such as dextran.

Figure 12:
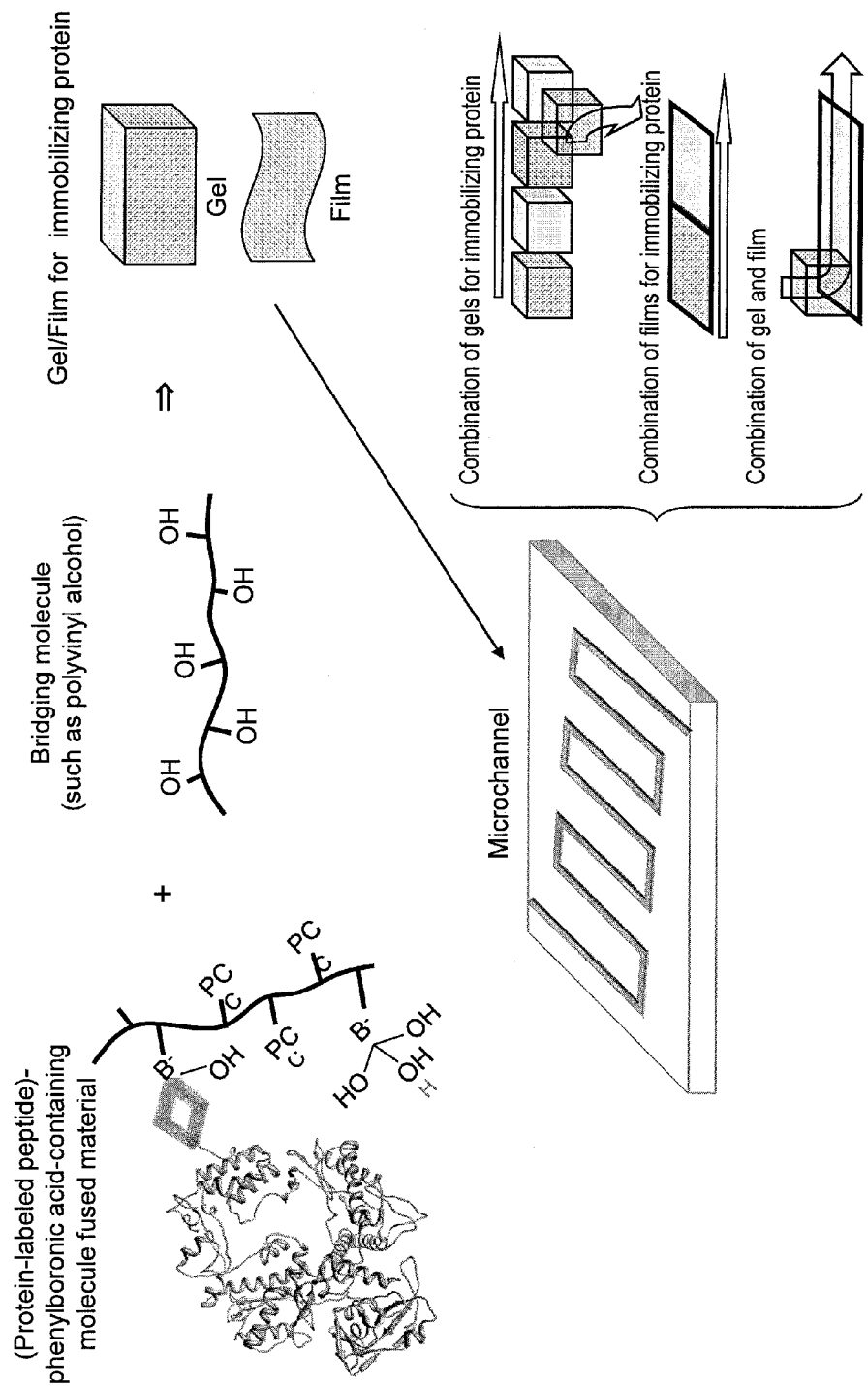
FIG. 12 illustrates an example of a measurement system using a device having a protein immobilized on an immobilization substrate (a gel or a film) formed by crosslinking a phenylboronic acid group-containing molecule.

Examples of the immobilization substrate that can be thus formed include a solid, a polymer membrane, a polymer semipermeable membrane, a film, a solid phase gel and a liquid phase gel. Accordingly, the present invention also provides a device in which a molecule (such as a protein molecule such as an enzyme) is stably immobilized via a covalent bond in a film-shaped substance such as a semipermeable membrane or a gel substance having various water contents (FIG. 12). Besides, such an immobilization substrate can be formed in a minute size of, for example, a micrometer or nanometer size.

Moreover, the label peptide sequence specifically recognizes and spontaneously binds to a phenylboronic acid group, and therefore, any protein can be immobilized on other various substances via a single phenylboronic acid group, or via a phenylboronic acid group immobilized in the form of a molecule in which the phenylboronic acid group and another chemical group coexist.

In order to allow a molecule attached to the label peptide sequence (namely, a labeled molecule) to be captured by the molecule having a phenylboronic acid group for immobilization, a labeled molecule solution mixed in an aqueous solution such as a buffer solution having a pH in the vicinity of a neutral pH is brought into contact with a solution containing the molecule having a phenylboronic acid group or the molecule having a phenylboronic acid group bound to a solid support, and the resultant is allowed to stand at 5 to 40 degrees C., preferably at room temperature, for several minutes to several tens minutes.

As described so far, when the label peptide sequence specifically and spontaneously binding to a phenylboronic acid group is attached to a molecule to be immobilized, on the basis of a bond between the phenylboronic acid group and the label peptide sequence, the molecule to be immobilized can be stably immobilized in any orientation on a solid support or in an immobilization substrate via the molecule having a phenylboronic acid group as a linker.

Furthermore, the present invention provides a molecule-immobilized device in which a molecule attached to the label peptide sequence is immobilized via a molecule having a phenylboronic acid group. In the molecule-immobilized device, the molecule attached to the label peptide sequence may be immobilized on a solid support via a molecule having a phenylboronic acid group, or the molecule attached to the label peptide sequence may be immobilized on an immobilization substrate formed by crosslinking a molecule having a phenylboronic acid group by a bridging molecule. The shape of the molecule-immobilized device is not especially limited as long as it contains the immobilized molecule, and may accord with the shape of the solid support, such as a substrate shape (a protein chip or the like) or particles (nanoparticles), or may accord with the shape of the immobilization substrate, such as a membrane, a film or a gel.

In the molecule-immobilized device of the present invention, a target molecule can be immobilized with the orientation controlled and/or in the form of a monomolecular layer, and therefore, the device is useful for various analyses of the molecule.

Accordingly, the present invention provides a sensor including a device having an immobilized target molecule; and means for detecting an intermolecular interaction. Here, the intermolecular interaction may be any interaction such as bond and dissociation as long as it is an interaction between the immobilized molecule and another molecule (of, for example, a test substance). The detecting means may be any of known detecting means including electric detecting means such as an FET and optical detecting means such as surface plasmon resonance. Now, typical examples will be described. Furthermore, FIGS. 11 and 12 illustrate examples of a measurement system using a device in which a protein is immobilized as the molecule.

A field-effect transistor (FET) is a technology widely used in a sensor employing electric detection. The principle is as follows: A current flowing from a source electrode to a drain electrode is controlled by a gate electrode working as a third electrode, and when an intermolecular interaction is caused on the surface of the gate electrode, the charge on the gate electrode is varied, and hence a current response is varied (FIG. 11).

The FET can perform highly sensitive detection if a reaction causing charge transfer occurs on a sensor chip, but the reaction should be caused in a position as close as possible to the surface of the gate electrode, and a distance allowable for the detection is said to be several nanometers. Therefore, if the device of the present invention in which molecules are immobilized with the highly controlled height and the controlled orientation is used as the gate electrode, the molecules can be controlled to align within a detection limit of several nanometers. Accordingly, the molecule-immobilized device of the present invention is useful for a sensor utilizing a highly sensitive FET.

Incidentally, proteins such as enzymes generally have a size of a several nanometer diameter, which is substantially equivalent to the detection limit of an FET. Therefore, the orientation control of a protein molecule attained by the present invention is effective means for producing a functional sensor for a field-effect transistor.

If the three-dimensional structure of a protein to be immobilized is known, the sequence control can be easily performed as intended, but even when the three-dimensional structure is unknown, the device can be optimized, in a trial-and-error manner, for the detection of a charge transfer reaction. In the present invention, since the label peptide sequence having phenylboronic acid binding capacity can be easily inserted to any position in a protein molecule, protein molecules having the label peptide sequence respectively attached to various positions can be prepared so that the reactions of the respective protein molecules can be easily checked.

The fabrication of the sensor includes, for example, (i) forming a monomolecular layer of a phenylboronic acid by causing a reaction of a thiolated phenylboronic acid group with a surface of a metal substrate or the like of gold, platinum or the like; and (ii) adding, onto the substrate, a solution containing a protein molecule having the label peptide sequence attached thereto via a linker sequence, thereby forming a sensor chip coated with a monomolecular layer of the protein molecule controlled in the orientation.

A surface plasmon resonance sensor is a sensor capable of analyzing an intermolecular interaction on a sensor chip on a real-time basis by utilizing the surface plasmon resonance. For example, a commercial surface plasmon resonance sensor (such as one manufactured by BIAcore Inc.) is easily available A target molecule is immobilized on a sensor chip in accordance with the method of the present invention, a microchannel is provided on the sensor chip, and a sample containing a test substance is supplied thereto at a constant flow rate. If an interaction is caused between the immobilized molecule and the test substance, bond and dissociation are optically detected owing to a surface plasmon phenomenon, so as to be monitored on a real-time basis in the form of a sensorgram. The surface plasmon resonance sensor has advantages that it can highly sensitively detect a minute amount of sample and the kinetics of an interaction can be analyzed on a real-time basis.

Reflectometry is a method for measuring the amount of protein adsorbed onto the surface of a sample holder by making a laser beam reflected on the sample holder and measuring reflected light. A reflectometry biosensor obtained by combining the principle of the reflectometry and a microfluidic chip is easily available A molecule is immobilized on a sensor chip in accordance with the method of the present invention, a microchannel is provided on the sensor chip, and a sample containing a test substance is supplied thereto at a constant flow rate. If an interaction is caused between the immobilized molecule and the test substance, the amount of adsorbed protein can be monitored on a real-time basis in the form of a sensorgram. The reflectometry biosensor has advantages of being highly sensitive for detecting a minute amount of sample and being capable of analyzing the kinetics of an interaction on a real-time basis.

If a molecule immobilized on an immobilization substrate in the form of a membrane, a film or a gel is used as the molecule-immobilized device, a plurality of molecule reactions, which could have been performed only by replacing solutions, can be performed by arranging minute gels in the molecule-immobilized device (FIG. 12), and such a device can be simply incorporated into a measurement apparatus.

Moreover, when the molecule-immobilized device of the present invention is in the form of particles (of a nano size or micro size), a membrane or a gel, it is useful for highly sensitive analysis performed within a microchannel.

Besides, when the molecule-immobilized device is in the form of particles, a molecule (a protein molecule) is immobilized on a particle and hence can be well dispersed in an aqueous solution, and therefore, can be efficiently reacted with a test substance. If complete dispersion is attained, particles are aggregated when an intermolecular interaction occurs, and therefore, a bond among molecules can be easily analyzed. Incidentally, such dispersibility is significant also in patterning nano particles by an ink jet method or a spray method.

EXAMPLES

Example 1

Search for Peptide Sequence Having Phenylboronic Acid Binding Capacity

Poly((2-methacryloyloxyethyl phosphorylcholine)-co-(n-butyl methacrylate)-co-(p-vinyl phenylboronic acid)) (hereinafter abbreviated as PMBV) was polymerized to have a composition of 60 mol % of 2-methacryloyloxyethyl phosphorylcholine group, 20 mol % of n-butyl methacrylic acid and 20 mol % of p-vinyl phenylboronic acid.

This PMBV was dissolved in a phosphate buffer physiological saline solution (PBS: 10 mM $NaH_2PO_4/Na_2HPO_4$, 150 mM NaCl, pH 7.3) to a concentration of 0.25 mg/ml, and 200 microliters of the resulting solution was dispensed into each well of a 96-well plate.

Figure 2:
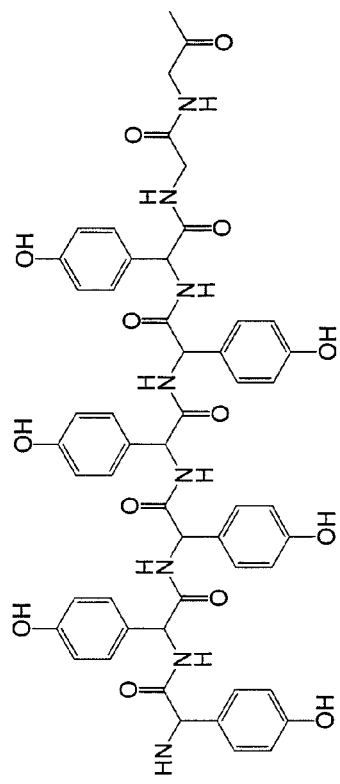
Figure 2:
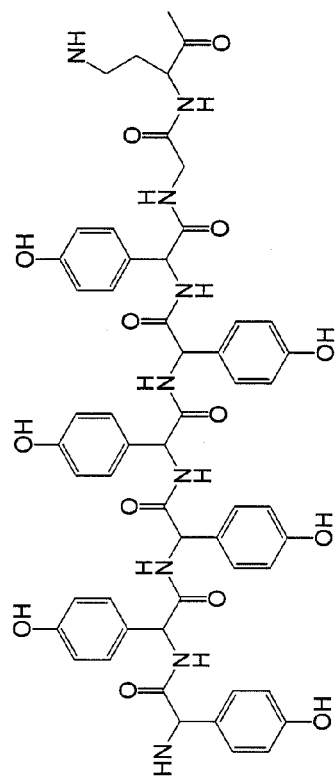
Figure 2:
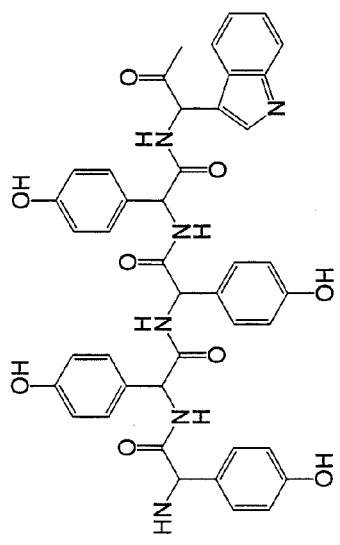
Figure 2:
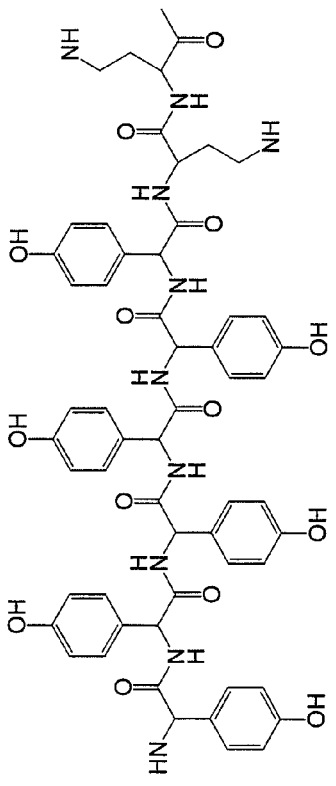

Into the wells containing the above-described solution, oligopeptides (in PBS) having chemical structural formulas illustrated in FIG. 2 were dispensed at a concentration of 0.05 mM in each well, followed by mixing. Specifically, the following oligopeptides were used:

```
                                         (SEQ ID NO: 1)
Tyr-Tyr-Tyr-Tyr-Tyr-Tyr (6Y)

(SEQ ID NO: 2)
Ser-Ser-Ser-Ser-Ser-Ser-Trp (6SW)

(SEQ ID NO: 3)
Ser-Ser-Ser-Ser-Trp (4SW)

(SEQ ID NO: 4)
Tyr-Tyr-Tyr-Tyr-Tyr-Tyr-Trp (6YW)

(SEQ ID NO: 5)
Tyr-Tyr-Tyr-Tyr-Trp (4YW)

(SEQ ID NO: 6)
Tyr-Tyr-Tyr-Tyr-Tyr-Tyr-Gly-Gly (6Y2G)

(SEQ ID NO: 7)
Tyr-Tyr-Tyr-Tyr-Tyr-Tyr-Lys-Lys (6Y2K)

(SEQ ID NO: 8)
Tyr-Tyr-Tyr-Tyr-Tyr-Tyr-Gly-Lys (6YGK)
```

The resulting well plate was shook at 25 degrees C. for 2 hours (700 rpm, TAITEC MBR-022UP).

Figure 3:
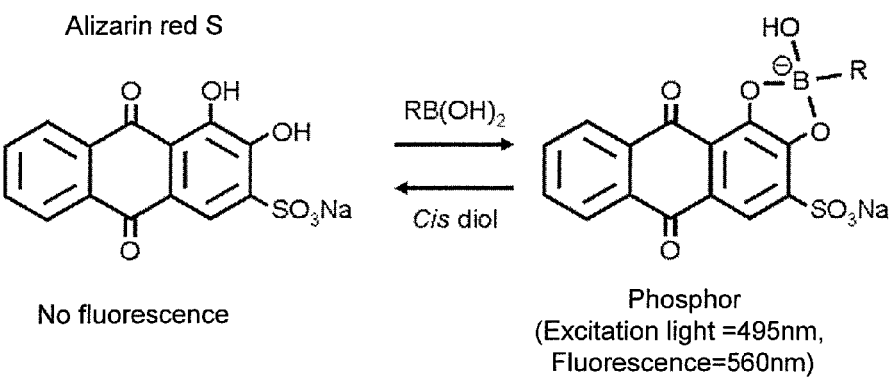
FIG. 3 illustrates a conceptual diagram of a structural formula of a phenylboronic acid-specifically binding dye (alizarin red S) used for screening for a peptide sequence binding to a phenylboronic acid group and a reaction for emitting fluorescence through a bond to a phenylboronic acid group (in FIG. 3A), and a chemical structural formula of a phenylboronic acid group-containing polymer (PMBV) used in Example 1 (in FIG. 3B).
Figure 3:
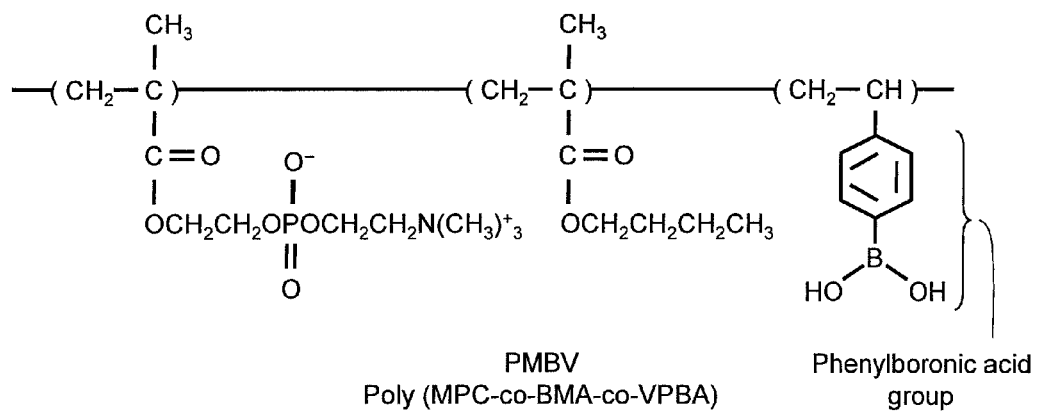

After the shaking, a fluorescent dye, alizarin red S, specifically binding to a phenylboronic acid group contained in the PMBV was dispensed into each well to a concentration of 0.05 mM in each well, followed by mixing. The molecular formula of the alizarin red S and the mechanism of emitting fluorescence when bound to phenylboronic acid are illustrated in FIG. 3A. The resulting well plate was shook at 25 degrees C. for 1 hour (700 rpm, TAITEC MBR-022UP).

In order to check how much the alizarin red S could bind to phenylboronic acid, the intensity of fluorescence derived from the alizarin red S was measured. A fluorospectrometer Gemini XS available from Molecular Devices Corp. was used for performing the fluorescence intensity measurement continuously at intervals of 10 nm in a range of 520 nm to 640 nm with exciting at an excitation wavelength of 495 nm, and the maximum value thus obtained was defined as the fluorescence intensity.

Figure 4:
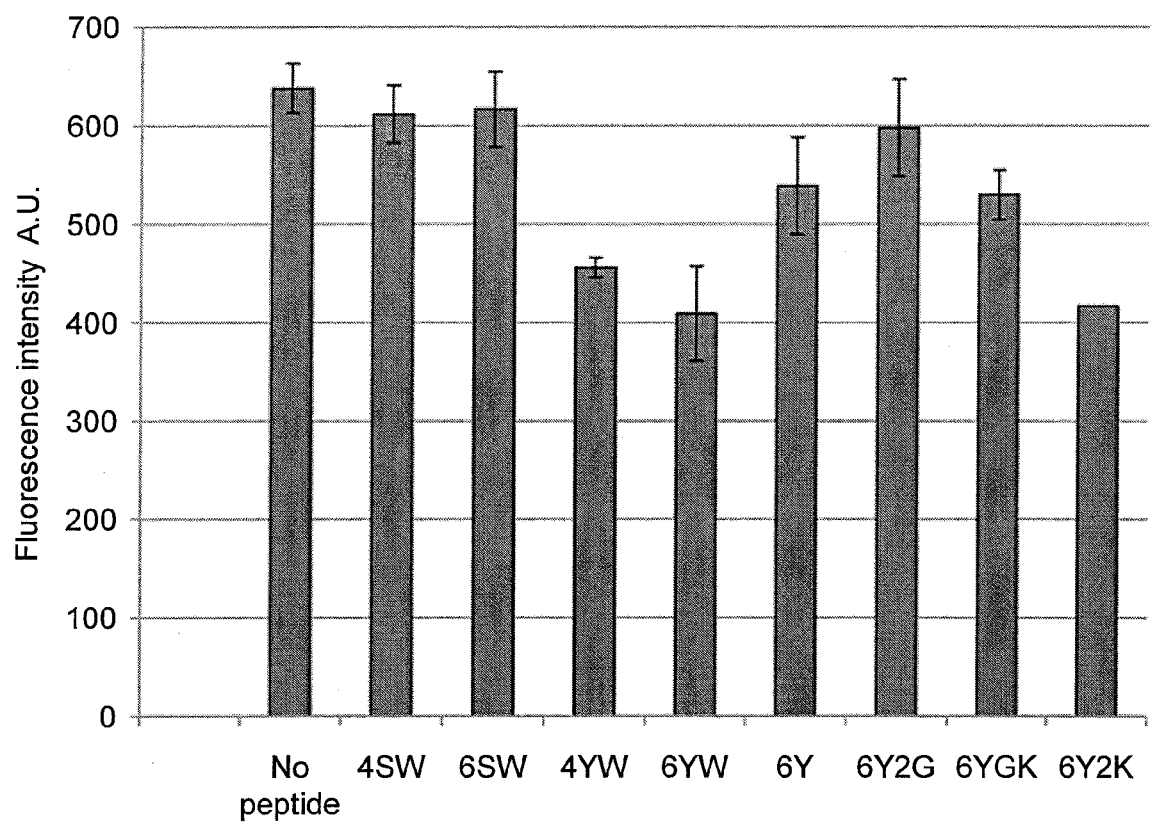
FIG. 4 is a bar chart illustrating how much the various synthetic peptides of FIG. 2 inhibit a reaction between the phenylboronic acid-specifically binding dye and a phenylboronic acid group, performed for screening for a peptide sequence binding to a phenylboronic acid group.

FIG. 4 illustrates a bar chart of maximum values of the fluorescence intensity derived from the alizarin red S obtained without or with adding the respective peptides. An error bar added to each bar represents a standard deviation obtained by three trials. As the bar is lower and the intensity of alizarin red S-derived fluorescence is lower, the corresponding peptide more inhibits the binding of the alizarin red S to a phenylboronic acid group, which suggests that the binding amount of the peptide to a phenylboronic acid group is large.

It was found, from the results shown in FIG. 4, that although all the oligopeptides bind to a phenylboronic acid group, the binding amount is particularly large in the oligopeptides 4YW, 6YW, 6Y, 6YGK and 6Y2K.

Example 2

Confirmation, by Surface Plasmon Resonance, of Bond Between Phenylboronic Acid and Peptide PMBV was prepared to have a composition of 25 mol % of 2-methacryloyloxyethyl phosphorylcholine group, 55 mol % of n-butyl methacrylic acid and 20 mol % of p-vinyl phenylboronic acid. Substrates for a surface plasmon resonance measuring apparatus were ultrasonic cleaned with ethanol for 5 minutes and naturally dried, and then, 40 microliters of a solution of 0.2 wt % PMBV in ethanol was dropped onto each of the substrates, and the resulting substrates were rotated at 1000 rpm for 30 seconds for spin coating. Thereafter, the substrates were dried under reduced pressure for 2 hours by using a desiccator (approximately 0.2 atmosphere).

Each of the substrates was closely adhered to a prism for the surface plasmon resonance measuring apparatus, which had been washed with acetone and dried, and the resulting prism was set in the surface plasmon resonance measuring apparatus (MORITEX, SPR-670M). Within the apparatus, the substrate was washed with a phosphate buffer physiological saline solution (10 mM $NaH_2PO_4/Na_2HPO_4$, 150 mM NaCl, pH 7.3) (30 microliters/min) until the sensorgram was stabilized.

Three peptides (that is, one synthetic peptide showing a low inhibiting effect for the reaction between the phenylboronic acid-specifically binding dye and the phenylboronic acid (6SW, SEQ ID NO: 2) and two synthetic peptides showing a high inhibiting effect for the reaction (6YW, SEQ ID NO: 4 and 6Y2K, SEQ ID NO: 7) in Example 1 were respectively dissolved in the same phosphate buffer physiological saline solution to a concentration of 1 mg/ml.

After confirming that the sensorgram was stabilized, each of the peptide solutions was allowed to flow on the substrate for 240 seconds (at 30 microliters/min), and thus, a binding curve of each peptide was obtained. Thereafter, a phosphate buffer physiological saline solution was allowed to flow on the substrate at the same flow rate, and thus, a dissociation curve of each peptide was obtained.

Figure 5:
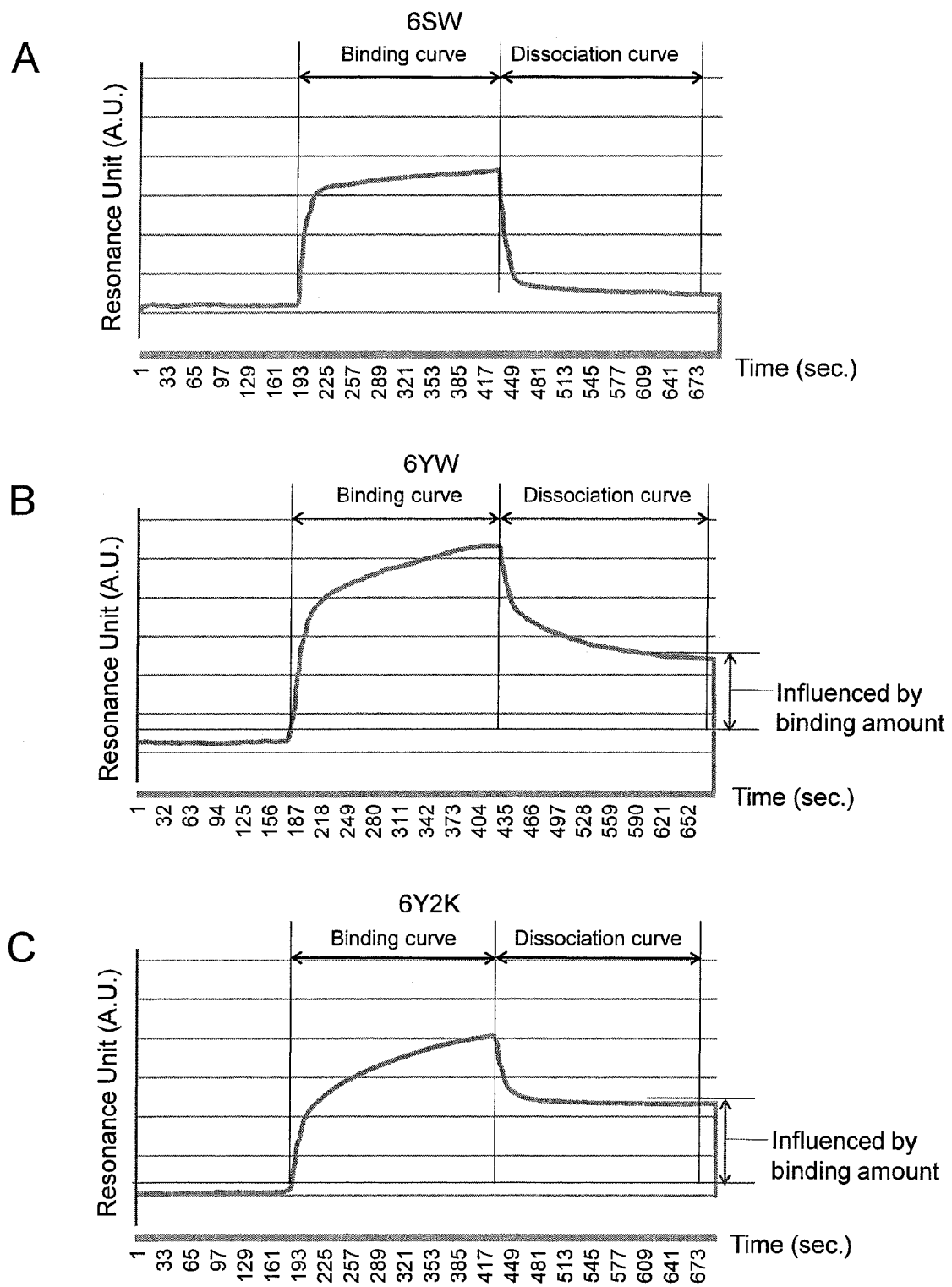
FIG. 5 illustrates sensorgrams for checking, by using surface plasmon resonance, interaction of synthetic peptides 6SW (in FIG. 5A), 6YW (in FIG. 5B) and 6Y2K (in FIG. 5C) on a chip surface-coated with a phenylboronic acid group-containing polymer.

FIG. 5 illustrates the thus obtained sensorgrams. With respect to the synthetic peptide 6SW (SEQ ID NO: 2) that showed a low inhibiting effect for the reaction between the phenylboronic acid-specifically binding dye and the phenylboronic acid in Example 1, it was found, from a rise in a binding curve portion (corresponding to a portion from the vicinity of 180 sec. to the vicinity of 420 sec.), that it has affinity with PMBV, but it was also found, from a rapid drop shown in a dissociation curve portion (corresponding to a portion following the vicinity of 420 sec.), that the bond to the PMBV is not very stable (FIG. 5A). In contrast, with respect to each of the synthetic peptides 6YW (SEQ ID NO: 4) and 6Y2K (SEQ ID NO: 7) that were found to have a high inhibiting effect for the reaction between the phenylboronic acid-specifically binding dye and the phenylboronic acid, the sensorgram did not drop to a background level in a dissociation curve portion, but showed a rise reflecting the binding amount as illustrated in FIGS. 5B and 5C. With respect to the peptide 6Y2K in particular, the sensorgram was stabilized immediately (in the vicinity of 470 sec.) in the dissociation curve portion at a level significantly higher than the background level and did not drop, which reveals that a very stable bond was formed (FIG. 5C).

The aforementioned results are highly consistent with the search results for peptide sequences having phenylboronic acid binding capacity performed in Example 1 by the experiment of inhibiting the reaction between the phenylboronic acid-specifically binding dye and the phenylboronic acid.

Example 3

Optimization of Peptide Sequence Having Phenylboronic Acid Binding Capacity

PMBV polymerized to have a composition of 60 mol % of 2-methacryloyloxyethyl phosphorylcholine group, 20 mol % of n-butyl methacrylic acid and 20 mol % of p-vinyl phenylboronic acid was dissolved in a phosphate buffer physiological saline solution (10 mM $NaH_2PO_4/Na_2HPO_4$, 150 mM NaCl, pH 7.3) to a concentration of 0.25 mg/ml, and 200 microliters of the resulting solution was dispensed into each well of a 96-well plate.

Figure 6:
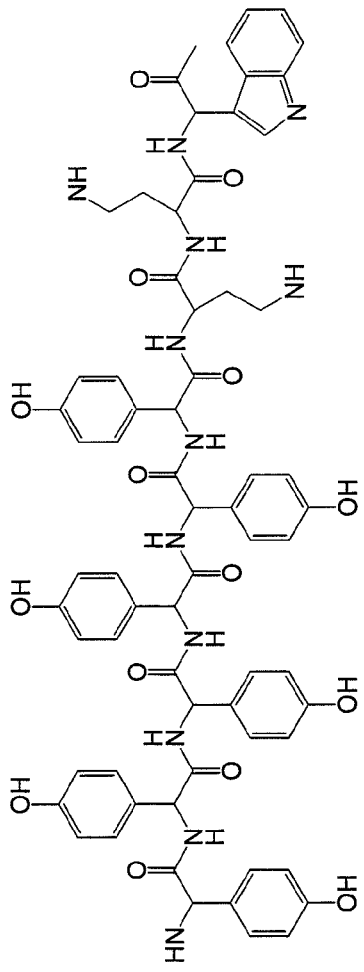
Figure 2:
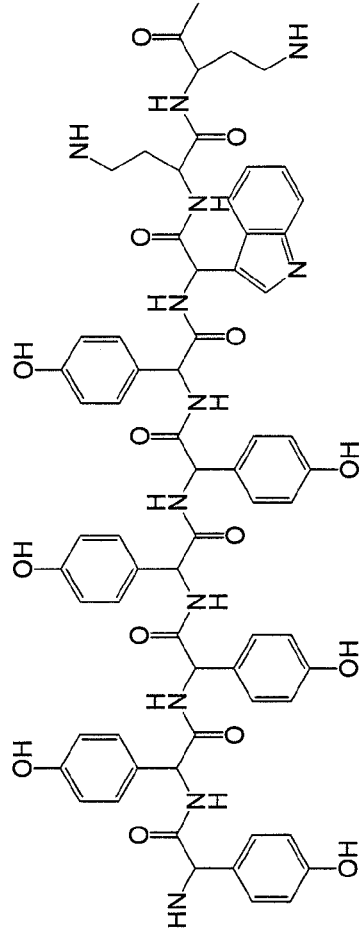

Into the respective wells containing the aforementioned solution, oligopeptides respectively having chemical structural formulas of FIG. 6 were dispensed to a concentration of 0.2 mM in each well (which was intentionally set to be lower than in Example 1), followed by mixing. Specifically, the following oligopeptides were used:

```
                                            (SEQ ID NO: 4)
Tyr-Tyr-Tyr-Tyr-Tyr-Tyr-Trp  (6YW)

(SEQ ID NO: 9)
Tyr-Tyr-Tyr-Tyr-Trp-Tyr-Tyr  (4YW2Y)

(SEQ ID NO: 10)
Tyr-Tyr-Tyr-Trp-Tyr-Tyr-Tyr  (3YW3Y)

(SEQ ID NO: 11)
Tyr-Tyr-Tyr-Tyr-Tyr-Trp-Tyr  (5YWY)

(SEQ ID NO: 12)
Tyr-Tyr-Tyr-Tyr-Tyr-Tyr-Lys-Lys-Trp  (6Y2KW)

(SEQ ID NO: 13)
Tyr-Tyr-Tyr-Tyr-Tyr-Tyr-Trp-Lys-Lys  (6YW2K)
```

The resulting well plate was shook at 25 degrees C. for 2 hours (700 rpm, TAITEC MBR-022UP).

After the shaking, a fluorescent dye, alizarin red S, specifically binding to a phenylboronic acid group contained in the PMBV was dispensed into each well to a concentration of 0.05 mM in each well, followed by mixing. The resulting well plate was shook at 25 degrees C. for 1 hour (700 rpm, TAITEC MBR-022UP).

In order to check how much the alizarin red S could bind to phenylboronic acid, the intensity of fluorescence derived from the alizarin red S was measured. A fluorospectrometer Gemini XS available from Molecular Devices Corp. was used for performing the fluorescence intensity measurement continuously at intervals of 10 nm in a range of 520 nm to 640 nm with exciting at an excitation wavelength of 495 nm, and the maximum value thus obtained was defined as the fluorescence intensity.

Figure 7:
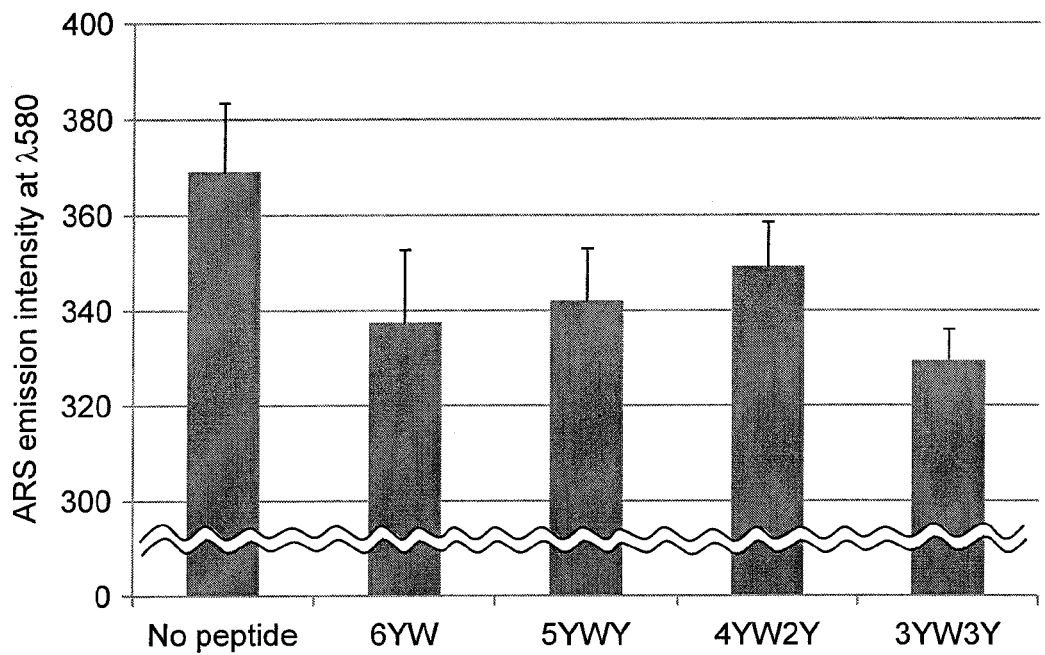
FIG. 7 is a bar chart illustrating how much the various synthetic peptides of FIG. 6 inhibit a reaction between a phenylboronic acid-specifically binding dye and a phenylboronic acid group, performed for optimizing a peptide sequence binding to a phenylboronic acid group.
Figure 7:
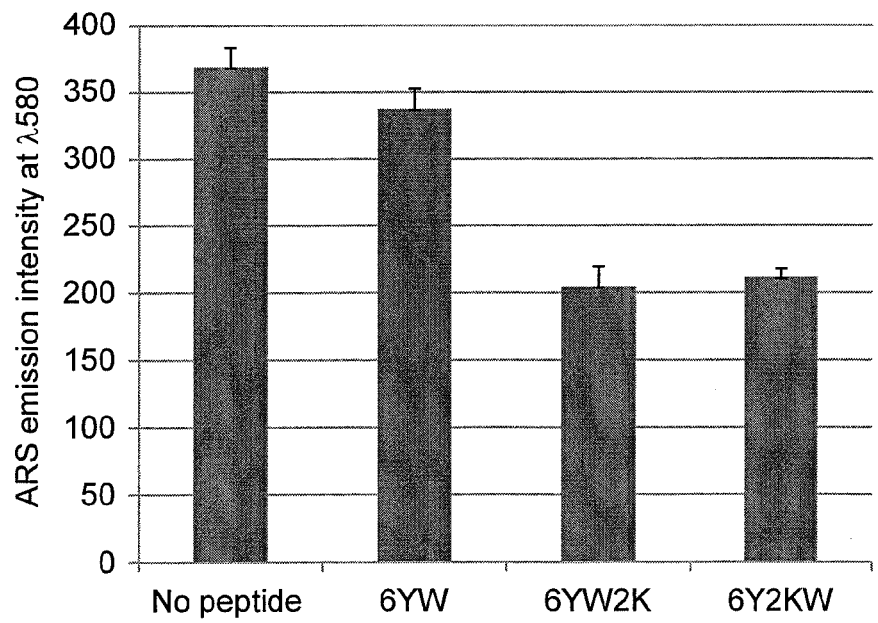

FIG. 7 illustrates a bar chart of maximum values of the fluorescence intensity derived from the alizarin red S obtained without or with adding the respective peptides. An error bar added to each bar represents a standard deviation obtained by three trials. It was revealed, from the chart of FIG. 7A, that the effect of a basic residue (particularly tryptophan) to increase the binding efficiency when added to a peptide sequence is not largely varied no matter where it is positioned in consecutive tyrosine residues. Furthermore, it was understood, from the chart of FIG. 7B, that the phenylboronic acid binding capacity can be additively increased when the two basic residues (lysine and tryptophan) that increase the binding efficiency when added to a peptide sequence are used in combination.

Example 4

Optimization of Composition of Phenylboronic Acid Group-Containing Polymer for Increasing Phenylboronic Acid Binding Capacity Since a peptide sequence having high phenylboronic acid binding capacity contains a basic residue, it can be presumed that increase of the local pH in the vicinity of a phenylboronic acid group in a solution largely affects the increase of the binding efficiency. Therefore, an experiment of inhibiting binding of the phenylboronic acid-specifically binding dye similar to that of Examples 1 and 3 was performed for examining whether or not a similar effect can be attained by newly introducing a basic residue not to a peptide sequence side but to a phenylboronic acid group-containing polymer side.

Figure 8:
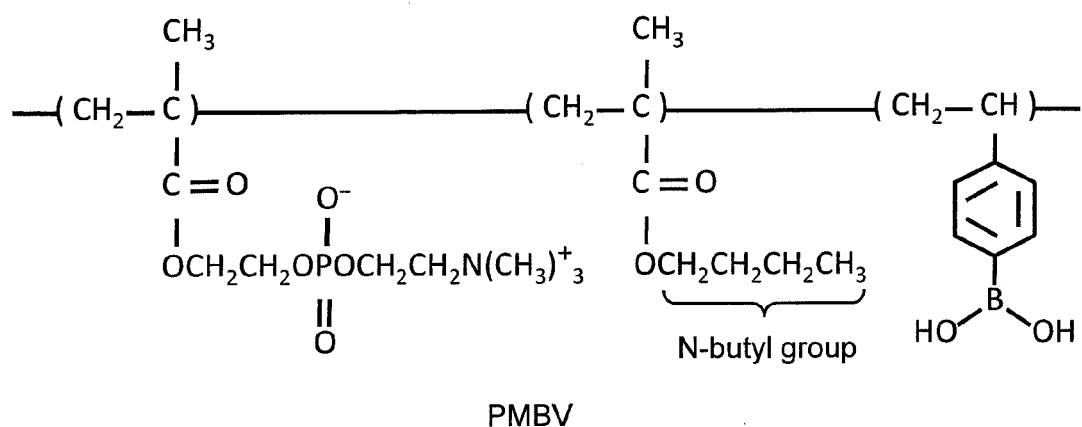
FIG. 8 illustrates a chemical structural formula of a phenylboronic acid group-containing polymer (PMBV) (in FIG. 8A) and a chemical structural formula of a phenylboronic acid group-containing polymer (PMDV) (in FIG. 8B).
Figure 8:
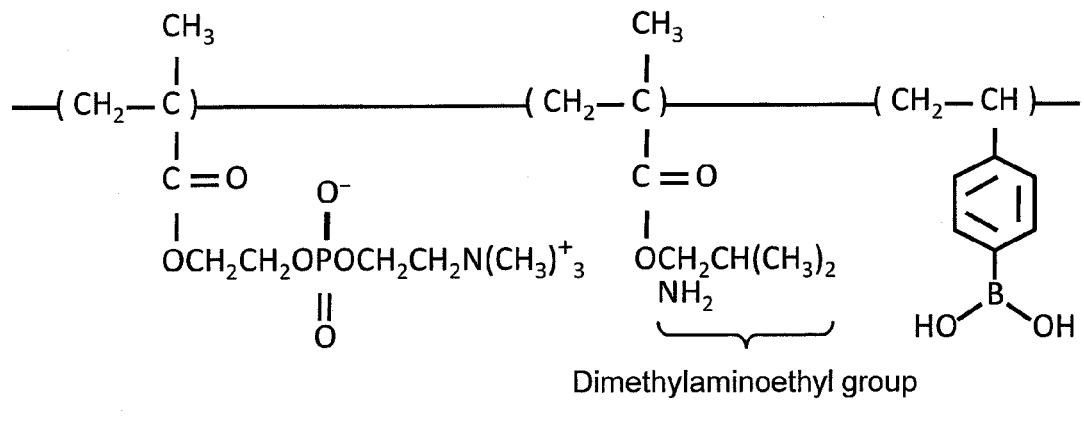

The PMBV was prepared in the same manner as in Example 1. Furthermore, poly((2-methacryloyloxyethyl phosphorylcholine)-co-(dimethylaminoethyl methacrylate)-co-(p-vinyl phenylboronic acid)) (hereinafter abbreviated as PMDV) was prepared to have a composition of 60 mol % of 2-methacryloyloxyethyl phosphorylcholine group, 20 mol % of dimethylaminoethyl methacrylic acid and 20 mol % of p-vinyl phenylboronic acid. The structures of the PMBV and the PMDV are illustrated in FIG. 8.

Two polymer solutions, that is, a solution of PMBV dissolved in a phosphate buffer physiological saline solution (10 mM $NaH_2PO_4/Na_2HPO_4$, 150 mM NaCl, pH 7.3) to a concentration of 0.25 mg/ml (a PMBV solution) and a solution of PMDV dissolved in the same saline solution to a concentration of 0.25 mg/ml (a PMDV solution), were prepared, and 200 microliters of each solution was dispensed into each well of a 96-well plate.

Into the wells containing the above-described solution, the oligopeptides (in PBS) (SEQ ID NOs: 1 to 8) having the chemical structural formulas illustrated in FIG. 2 were dispensed to a concentration of 0.2 mM in each well, followed by mixing.

The resulting well plate was shook at 25 degrees C. for 1 hour (700 rpm, TAITEC MBR-022UP). Incidentally, the peptide concentration and the shaking time were both set to make the inhibiting effect lower. After the shaking, a fluorescent dye, alizarin red S, specifically binding to a phenylboronic acid group contained in the polymer was dispensed into each well to a concentration of 0.05 mM in each well, followed by mixing. The resulting well plate was shook at 25 degrees C. for 1 hour (700 rpm, TAITEC MBR-022UP).

In order to check how much the alizarin red S could bind to phenylboronic acid, the intensity of fluorescence derived from the alizarin red S was measured. A fluorospectrometer Gemini XS available from Molecular Devices Corp. was used for performing the fluorescence intensity measurement continuously at intervals of 10 nm in a range of 520 nm to 640 nm with exciting at an excitation wavelength of 495 nm, and the maximum value thus obtained was defined as the fluorescence intensity.

Figure 9:
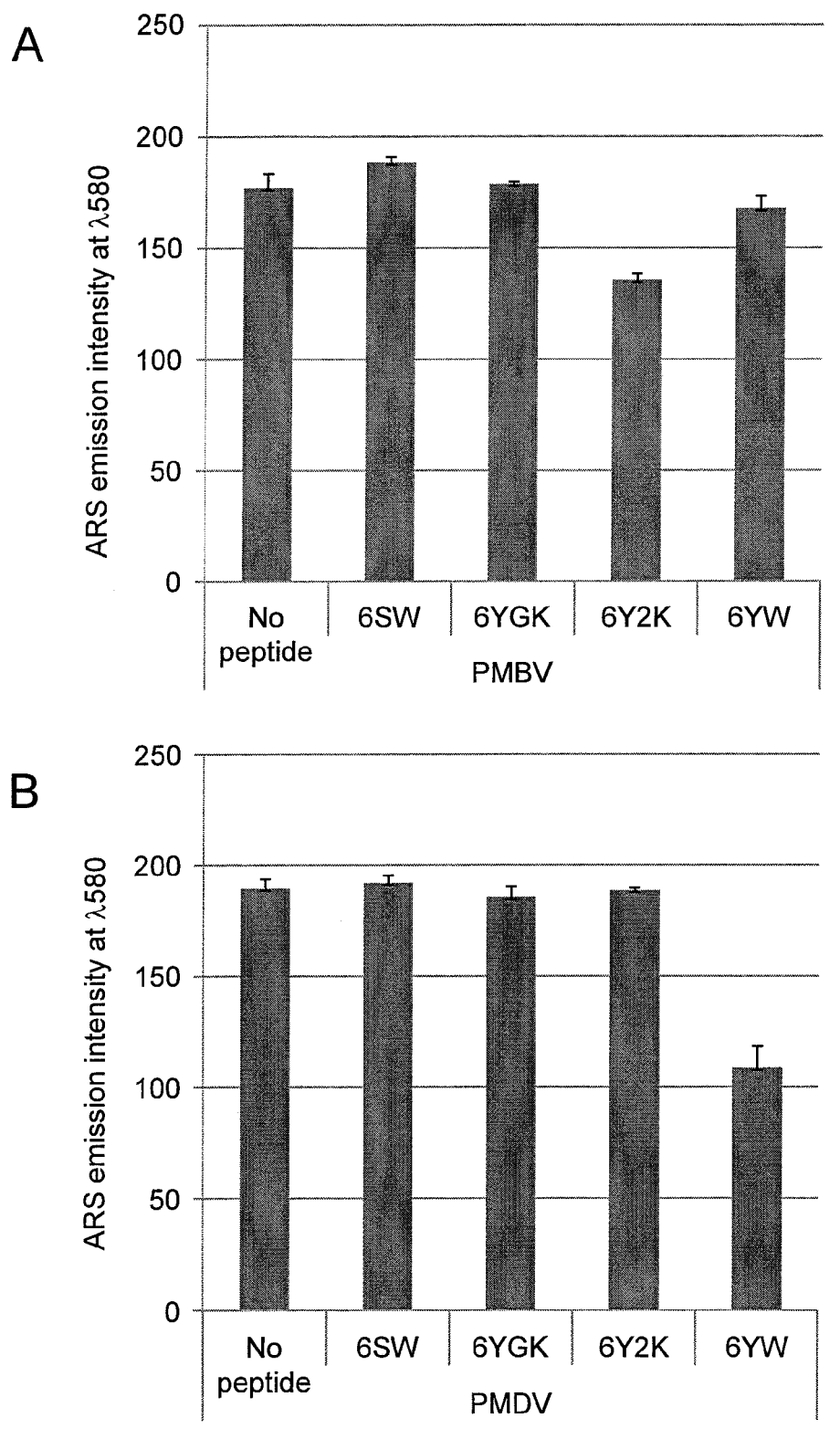

FIG. 9 illustrates a bar chart of maximum values of the fluorescence intensity derived from the alizarin red S obtained without or with adding the respective peptides. An error bar added to each bar represents a standard deviation obtained by three trials. As the bar is lower and the intensity of alizarin red S-derived fluorescence is lower, the corresponding peptide more inhibits binding of the alizarin red S to a phenylboronic acid group, which suggests that the binding amount of the peptide to a phenylboronic acid group is large. As a result, it could be confirmed that when the PMDV polymer having a basic functional group (a dimethylamino group) introduced therein is used, the peptide sequence 6Y2K (SEQ ID NO: 7) showing high binding efficiency to the PMBV in Example 1 showed a slight inhibiting effect for the binding of the dye but the peptide sequence 6YW (SEQ ID NO: 4) showed an extremely high inhibiting effect for the binding of the dye. Thus, it was revealed that selectivity for a peptide sequence to be bound is increased and the binding efficiency to phenylboronic acid is remarkably increased in using the PMDV than in using the PMBV.

Example 5

Figure 13:
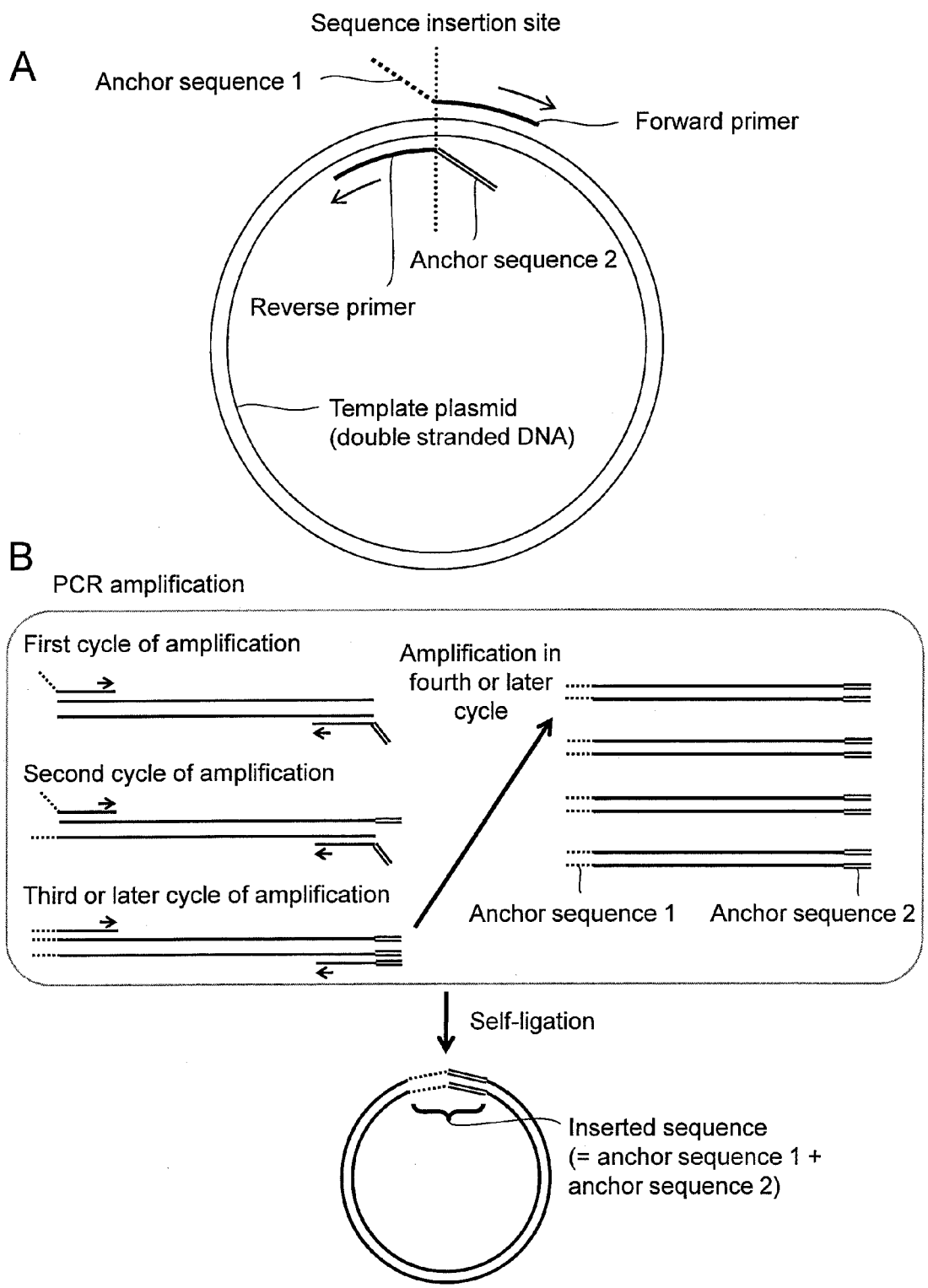
FIG. 13 illustrates a construction example of an expression vector used for producing a fusion protein having a label peptide sequence (in FIG. 13A), and a step of introducing the label peptide sequence by using the expression vector (in FIG. 13B).

Construction of Plasmid Encoding Luciferase Having Peptide Sequence with Phenylboronic Acid Binding Capacity Introduced Therein By using a pURE2 Luc plasmid, that is, a luciferase (hereinafter abbreviated as Luc) expression plasmid, as a template, the peptide sequences 6Y2K (SEQ ID NO: 7) and 6YW (SEQ ID NO: 4) were introduced into protein molecules at the C-terminal via 4 glycine residues. As an introduction method into the plasmid, inverse PCR was employed. The outline of this method is illustrated in FIGS. 13A and 13B. In the inverse PCR, primers are selected to be set in a back-to-back manner based on a sequence insertion site of a circular DNA (FIG. 13A). At this point, sequences to be introduced are added as anchor sequences 1 and 2 to the respective primers (FIG. 13A). When the PCR reaction is carried out under these conditions, a linear double stranded DNA to the ends of which the anchor sequences 1 and 2 are added is produced. When this DNA is ligated by a self-ligation reaction, a circular double stranded DNA having the anchor sequences inserted in desired sites can be obtained (FIG. 13B).

As for the primers, a sequence 5'TATTATTATAAAAAAT-AGCATATGAAGCTTTAGCATAACCCCTT-3' (SEQ ID NO: 14) was used as the forward primer for the 6Y2K, a sequence 5'-TATTATTATTGGTAGCATATGAAGCTT-TAGCATAACCCCTT-3' (SEQ ID NO: 15) was used as the forward primer for the 6YW, and a sequence 5'-ATAATAATAACCACCACCACCCAATTTG-GACTTTCCGCCCT-3' (SEQ ID NO: 16) was used as the common reverse primer.

An inverse PCR reaction solution was prepared by mixing 20 fmol of the template plasmid pURE2 Luc, 15 pmol each of the forward primer and the reverse primer, 2.5 U of KOD-Plus DNA polymerase (Toyobo Co., Ltd.), 5 microliters of 10×KOD buffer and 5 microliters of 10 mM dNTP, and adjusting the resulting mixture with dH₂O to obtain a total amount of 50 microliters. For the amplification reaction, after a reaction at 95 degrees C. for 1 minute, a cycle reaction was performed by 30 cycles of 98 degrees C. for 30 seconds, 55 degrees C. for 1 minute and 68 degrees C. for 4 minutes, and then the reaction solution was cooled to 4 degrees C.

Fifty microliters of the sample was collected, 1 microliter of DpnI (20 U/microliter, NEB Inc.) was added thereto, and a reaction was carried out at 37 degrees C. for 1 hour, so as to decompose the template plasmid. To the solution resulting from the reaction, 150 microliters of ethanol and 5 microliters of NaOAC were added, and the resulting solution was centrifuged at 4 degrees C. at 15000 rpm for 30 minutes, and the supernatant was discarded (ethanol precipitation).

Ten microliters of the precipitate was dissolved in dH₂O and mixed with 1 microliter of T4 kinase (Takara Bio Inc.) and 14 microliters of Ligation High (Toyobo Co., Ltd.), and the thus obtained mixture was reacted at 37 degrees C. for 1 hour. To the reaction solution, 5 microliters of Ligation High was further added, and the resulting solution was reacted at 4 degrees C. for 1 hour for causing self ligation.

Five microliters of the self-ligation reaction solution was mixed with 50 microliters of Competent Cell JM109 (Takara Bio Inc.), the resulting solution was allowed to stand still on ice for 10 minutes and then subjected to heat shock at 42 degrees C. for 45 seconds for transforming *E. coli*. The solution was inoculated in an LB-amp (LB broth: Invitrogen Corp., agar: Wako Pure Chemical Industries Ltd., ampicillin: SIGMA) plate, and cultured at 37 degrees C. overnight for allowing *E. coli* colonies to be formed. Some colonies were picked up to be cultured overnight in a 20 mL LB-amp culture medium and harvested, and plasmids were extracted and purified by using Plasmid Miniprep system (Marligen Biosciences Inc.). The purified plasmids were sequenced, and a plasmid in which the sequence insertion was confirmed was stored.

Example 6

Purification of Luciferase Having Peptide Sequence with Phenylboronic Acid Binding Capacity Introduced Therein One microliter of each of a plasmid (Luc6Y2K) having the sequence 6Y2K (SEQ ID NO: 7) introduced to the C-terminal of Luc and a plasmid (Luc6YW) having the sequence 6YW (SEQ ID NO: 4) introduced to the C-terminal of Luc, each in 100 ng/microliter, was added to 50 microliters of Competent Cell BL21 for protein expression (Novagen Inc.), and the resulting solution was allowed to stand still at 4 degrees C. for 10 minutes and then subjected to heat shock at 42 degrees C. for 30 seconds for causing transformation. The resulting solution was inoculated in an LB-amp (LB broth: Invitrogen Corp., agar: Wako Pure Chemical Industries Ltd., ampicillin: SIGMA) plate, and cultured at 37 degrees C. overnight for allowing *E. coli* colonies to be formed. Some colonies were picked up to be cultured overnight at 25 degrees C. in a 2 L LB-amp culture medium and harvested.

The bacterial cells were suspended in a cell membrane homogenate and mixed with gentle rotation at room temperature for 10 minutes, and then, the resultant was centrifuged (30,000 g, 30 minutes) and the supernatant was recovered. Since the plasmids Luc-6Y2K and Luc-6YW both have a Strep-tag sequence on the N terminal side, affinity chromatography purification utilizing avidin-biotin interaction was performed by using AKTA explorer 10S system. The centrifuged supernatant having been filtered by a 0.1 micrometer filter was poured into Strep Trap HP 5 ml (GE Healthcare Japan) at a flow rate of 5 ml/min for performing sample adsorption. After the sample adsorption, the column was washed with 10 ml of phosphate buffer physiological saline solution (10 mM $NaH_2PO_4$/$Na_2HPO_4$, 150 mM NaCl, pH 7.3). A phosphate buffer physiological saline solution containing desthiobiotin (Sigma Aldrich) dissolved therein was used for eluting a target protein adsorbed onto the column. The eluent sample was subjected to SDS polyacrylamide electrophoresis for each fraction to confirm that the target protein was expressed and that the other contaminant proteins were removed.

It is noted that the present invention is not limited to the aforementioned examples but embraces a variety of modifications. For example, the aforementioned examples are described in detail so that the present invention can be easily understood, and therefore, the invention is not limited to the construction including all the described elements. Furthermore, a part of the construction of a given example can be replaced by the construction of another example, or the construction of one example can be added to the construction of another example. Moreover, the construction of one example can be added to, deleted from or replaced by a part of the construction of another example.

The contents of all the publications, patents and patent applications cited herein are incorporated herein by reference.

SEQUENCE FREE TEXT

SEQ ID NOs: 1 to 13: artificial sequences (synthetic oligopeptides)

SEQ ID NOs: 14 to 16: artificial sequences (synthetic oligonucleotides)

The invention claimed is:

1. A method for immobilizing a molecule, comprising the steps of:

attaching a label peptide sequence comprising two or more amino acid residues of hydroxyl group-containing amino acids, and one to three amino acid residues selected from the group consisting of amino acid residues of basic amino acids and tryptophan residue to a molecule to form a labeled molecule;

providing a molecule having a phenylboronic acid group with one or more functional groups bound to a solid support or crosslinked by a bridging molecule to form an immobilization substrate; and bringing the molecule having a phenylboronic acid group into contact with the labeled molecule, to bind and immobilize the labeled molecule by the molecule having a phenylboronic acid group.

2. The method according to claim 1, wherein the hydroxyl group-containing amino acids are one or more selected from the group consisting of serine, threonine and tyrosine.

3. The method according to claim 1, wherein the basic amino acids are one or more selected from the group consisting of lysine and arginine.

4. The method according to claim 1, wherein the label peptide sequence is 4 to 6 amino acid residues and comprises at least one of 4 to 6 consecutive amino acid residues of hydroxyl group-containing amino acids, or a combination of 3 to 5 amino acid residues of hydroxyl group containing amino acids and 1 to 3 amino acid residues selected from the group consisting of amino acid residues of basic amino acids and tryptophan residue.

5. The method according to claim 1, wherein the label peptide sequence is 7 or more amino acid residues and comprises at least one of 7 or more consecutive amino acid residues of hydroxyl group-containing amino acids, or a combination of 4 or more amino acid residues of hydroxyl group containing amino acids and 1 to 3 amino acid residues selected from the group consisting of amino acid residues of basic amino acids and tryptophan residue.

6. The method according to claim 1, wherein the molecule to which the label peptide is attached is a protein.

7. The method according to claim 1, wherein the label peptide sequence is attached to the molecule via a covalent bond in a position away from an active site or a recognition region of the molecule.

8. The method according to claim 1, wherein the molecule having a phenylboronic acid group is a polymer having two or more phenylboronic acid groups.

9. The method according to claim 1, wherein the molecule having a phenylboronic acid group is poly((2-methacryloyloxyethyl phosphorylcholine)-co-(n-butyl methacrylate)-co-(p-vinyl phenylboronic acid)) or poly((2-methacryloyloxyethyl phosphorylcholine)-co-(dimethylaminoethyl methacrylate)-co-(p-vinyl phenylboronic acid)).

10. The method according to claim 1, wherein the molecule having a phenylboronic acid group is bound to a solid support.

11. The method according to claim 1, wherein the molecule having a phenylboronic acid group is bound to a surface of a solid support and the labeled molecule is immobilized on the surface of the solid support.

12. The method according to claim 11, wherein the labeled molecule is immobilized as a monomolecular layer held on the surface of the solid support in the same orientation.

13. The method according to claim 10, wherein the molecule having a phenylboronic acid group comprises a phenylboronic acid group and a headgroup, and the headgroup is a functional group capable of covalently binding to the solid support.

14. The method according to claim 10, wherein the solid support is a noble metal.

15. The method according to claim 14, wherein the noble metal is selected from the group consisting of silver, gold, platinum and palladium.

16. The method according to claim 10, wherein the solid support is an electrode.

17. The method according to claim 10, wherein the solid support is a plastic.

18. The method according to claim 17, wherein the plastic is selected from the group consisting of polycarbonate, polyethylene, polypropylene, polystyrene, polyvinyl chloride and polyethylene terephthalate.

19. The method according to claim 1, wherein the molecule having a phenylboronic acid group is crosslinked by a bridging molecule to form an immobilization substrate, and the labeled molecule is immobilized on the immobilization substrate.

20. The method according to claim 19, wherein the bridging molecule is polyhydric alcohol.

21. The method according to claim 20, wherein the polyhydric alcohol is polyvinyl alcohol.

22. The method according to claim 19, wherein the immobilization substrate is one or more selected from the group consisting of a solid, a polymer membrane, a polymer semipermeable membrane, a film, a solid phase gel and a liquid phase gel.

23. The method according to claim 1, wherein the label peptide sequence comprises an amino acid sequence of SEQ ID NO: 4 or SEQ ID NO: 7.

24. The method according to claim 1, wherein the molecule having a phenylboronic acid group is crosslinked by a bridging molecule to form an immobilization substrate.

\* \* \* \* \*

SEQUENCE LISTING

```
<160> NUMBER OF SEQ ID NOS: 16

<210> SEQ ID NO 1
<211> LENGTH: 6
<212> TYPE: PRT
<213> ORGANISM: Artificial
<220> FEATURE:
<223> OTHER INFORMATION: synthetic oligopeptide

<400> SEQUENCE: 1

Tyr Tyr Tyr Tyr Tyr Tyr
1               5

<210> SEQ ID NO 2
<211> LENGTH: 7
<212> TYPE: PRT
<213> ORGANISM: Artificial
<220> FEATURE:
<223> OTHER INFORMATION: synthetic oligopeptide

<400> SEQUENCE: 2

Ser Ser Ser Ser Ser Ser Trp
1               5

<210> SEQ ID NO 3
<211> LENGTH: 5
<212> TYPE: PRT
<213> ORGANISM: Artificial
<220> FEATURE:
<223> OTHER INFORMATION: synthetic oligopeptide

<400> SEQUENCE: 3

Ser Ser Ser Ser Trp
1               5

<210> SEQ ID NO 4
<211> LENGTH: 7
<212> TYPE: PRT
<213> ORGANISM: Artificial
<220> FEATURE:
<223> OTHER INFORMATION: synthetic oligopeptide

<400> SEQUENCE: 4

Tyr Tyr Tyr Tyr Tyr Tyr Trp
1               5

<210> SEQ ID NO 5
<211> LENGTH: 5
<212> TYPE: PRT
<213> ORGANISM: Artificial
```

```
<220> FEATURE:
<223> OTHER INFORMATION: synthetic oligopeptide

<400> SEQUENCE: 5

Tyr Tyr Tyr Tyr Trp
1               5

<210> SEQ ID NO 6
<211> LENGTH: 8
<212> TYPE: PRT
<213> ORGANISM: Artificial
<220> FEATURE:
<223> OTHER INFORMATION: synthetic oligopeptide

<400> SEQUENCE: 6

Tyr Tyr Tyr Tyr Tyr Tyr Gly Gly
1               5

<210> SEQ ID NO 7
<211> LENGTH: 8
<212> TYPE: PRT
<213> ORGANISM: Artificial
<220> FEATURE:
<223> OTHER INFORMATION: synthetic oligopeptide

<400> SEQUENCE: 7

Tyr Tyr Tyr Tyr Tyr Tyr Lys Lys
1               5

<210> SEQ ID NO 8
<211> LENGTH: 8
<212> TYPE: PRT
<213> ORGANISM: Artificial
<220> FEATURE:
<223> OTHER INFORMATION: synthetic oligopeptide

<400> SEQUENCE: 8

Tyr Tyr Tyr Tyr Tyr Tyr Gly Lys
1               5

<210> SEQ ID NO 9
<211> LENGTH: 7
<212> TYPE: PRT
<213> ORGANISM: Artificial
<220> FEATURE:
<223> OTHER INFORMATION: synthetic oligopeptide

<400> SEQUENCE: 9

Tyr Tyr Tyr Tyr Trp Tyr Tyr
1               5

<210> SEQ ID NO 10
<211> LENGTH: 7
<212> TYPE: PRT
<213> ORGANISM: Artificial
<220> FEATURE:
<223> OTHER INFORMATION: synthetic oligopeptide

<400> SEQUENCE: 10

Tyr Tyr Tyr Trp Tyr Tyr Tyr
1               5

<210> SEQ ID NO 11
<211> LENGTH: 7
<212> TYPE: PRT
<213> ORGANISM: Artificial
<220> FEATURE:
```

```
<223> OTHER INFORMATION: synthetic oligopeptide

<400> SEQUENCE: 11

Tyr Tyr Tyr Tyr Tyr Trp Tyr
1               5

<210> SEQ ID NO 12
<211> LENGTH: 9
<212> TYPE: PRT
<213> ORGANISM: Artificial
<220> FEATURE:
<223> OTHER INFORMATION: synthetic oligopeptide

<400> SEQUENCE: 12

Tyr Tyr Tyr Tyr Tyr Tyr Lys Lys Trp
1               5

<210> SEQ ID NO 13
<211> LENGTH: 9
<212> TYPE: PRT
<213> ORGANISM: Artificial
<220> FEATURE:
<223> OTHER INFORMATION: synthetic oligopeptide

<400> SEQUENCE: 13

Tyr Tyr Tyr Tyr Tyr Tyr Trp Lys Lys
1               5

<210> SEQ ID NO 14
<211> LENGTH: 44
<212> TYPE: DNA
<213> ORGANISM: Artificial
<220> FEATURE:
<223> OTHER INFORMATION: synthetic oligonucleotide

<400> SEQUENCE: 14
tattattata aaaaatagca tatgaagctt tagcataacc cctt                    44

<210> SEQ ID NO 15
<211> LENGTH: 41
<212> TYPE: DNA
<213> ORGANISM: Artificial
<220> FEATURE:
<223> OTHER INFORMATION: synthetic oligonucleotide

<400> SEQUENCE: 15
tattattatt ggtagcatat gaagctttag cataaccccct t                      41

<210> SEQ ID NO 16
<211> LENGTH: 41
<212> TYPE: DNA
<213> ORGANISM: Artificial
<220> FEATURE:
<223> OTHER INFORMATION: synthetic oligonucleotide

<400> SEQUENCE: 16
ataataataa ccaccaccac ccaatttgga ctttccgccc t                       41
```